US007455248B2

(12) United States Patent
Kablik et al.

(10) Patent No.: US 7,455,248 B2
(45) Date of Patent: Nov. 25, 2008

(54) POWDER DELIVERY DEVICE

(75) Inventors: Joseph J. Kablik, Tyngsborough, MA (US); Andrew Gentile, Allston, MA (US); A. David Boccuti, Arlington, MA (US)

(73) Assignee: Genzyme Corporation, Cambridge, MA (US)

( * ) Notice: Subject to any disclaimer, the term of this patent is extended or adjusted under 35 U.S.C. 154(b) by 659 days.

(21) Appl. No.: 11/084,651

(22) Filed: Mar. 17, 2005

(65) Prior Publication Data

US 2005/0205087 A1 Sep. 22, 2005

Related U.S. Application Data

(60) Provisional application No. 60/554,009, filed on Mar. 17, 2004.

(51) Int. Cl.
*A01C 3/06* (2006.01)

(52) U.S. Cl. ....................... 239/654; 239/650; 239/362; 239/363; 239/526

(58) Field of Classification Search ......... 222/631–633; 239/310–318, 329, 330, 337, 346, 355, 361–363, 239/373, 375–378, 526, 650, 654; 128/200.23; 604/58, 61
See application file for complete search history.

(56) References Cited

U.S. PATENT DOCUMENTS

| | | | | |
|---|---|---|---|---|
| 204,469 | A * | 6/1878 | Weed | 239/362 |
| 283,341 | A * | 8/1883 | Schmitt et al. | 144/78 |
| 401,355 | A * | 4/1889 | Kneuper | 239/327 |
| 1,776,489 | A * | 9/1930 | Cobb | 222/633 |
| 2,014,671 | A * | 9/1935 | Rothe | 239/362 |

(Continued)

FOREIGN PATENT DOCUMENTS

EP 0193510 11/1988

(Continued)

OTHER PUBLICATIONS

*A Minefield Marking Device*, Demining Research at The University of Western Australia, demining@mech.uwa.edu.au, pp. 1-4.

(Continued)

*Primary Examiner*—Len Tran
*Assistant Examiner*—Jason J Boeckmann
(74) *Attorney, Agent, or Firm*—Richard D. Allison; Thomas J. DesRosier

(57) ABSTRACT

A pistol-shaped powder delivery device consolidates propellant pulse creation, powder storage, powder aerosolization and aerolsolized powdered delivery in a single device while providing dose, pattern and coverage control of the output spray. The single-hand-held, single-hand-operated device includes a housing having a handle portion that is selectively collapsed to generate a propellant pulse that is conveyed into and through powder stored in a reservoir mounted at an upward angle to the horizontal in a receptacle provided in the housing. Powder in the reservoir is caused to be aerosolized by the propellant pulse whereupon aerosolized powder exits the reservoir through an open end of, and elongate slots provided in the sidewall of, an elongate hollow member extending from an outlet in the receptacle through the stored powdered material into a head space in the reservoir. The outlet is connected a barrel portion for output of the aerosolized powder spray.

23 Claims, 5 Drawing Sheets

U.S. PATENT DOCUMENTS

| | | | | |
|---|---|---|---|---|
| 2,064,726 | A * | 12/1936 | Brown | 239/350 |
| 2,349,894 | A * | 5/1944 | Wells | 239/350 |
| 2,357,979 | A * | 9/1944 | Schmitt et al. | 239/362 |
| 3,042,667 | A | 7/1962 | Vanderhoff et al. | |
| 3,669,113 | A | 6/1972 | Altounyan et al. | |
| 4,091,966 | A | 5/1978 | Laauwe | 222/211 |
| 4,286,735 | A | 9/1981 | Sneider | 222/189 |
| 4,356,941 | A | 11/1982 | McRoskey et al. | 222/632 |
| 4,582,865 | A | 4/1986 | Balazs et al. | |
| 4,730,751 | A | 3/1988 | Mackles et al. | 222/189 |
| 4,861,405 | A | 8/1989 | Kassai | |
| 5,156,307 | A | 10/1992 | Callahan et al. | 222/189 |
| 5,261,895 | A | 11/1993 | Kablik | |
| 5,273,527 | A | 12/1993 | Schatz et al. | |
| 5,328,099 | A | 7/1994 | Petit et al. | 239/372 |
| 5,760,200 | A | 6/1998 | Miller et al. | |
| 5,884,621 | A | 3/1999 | Matsugi et al. | 128/203.15 |
| 5,893,484 | A | 4/1999 | Fuchs et al. | 222/83 |
| 5,894,967 | A | 4/1999 | Stahley et al. | 222/633 |
| 6,030,958 | A | 2/2000 | Burns et al. | |
| 6,214,331 | B1 | 4/2001 | Vanderhoff et al. | |
| 6,235,726 | B1 | 5/2001 | Burns et al. | |
| 6,257,786 | B1 * | 7/2001 | Thomas | 401/43 |
| 6,332,461 | B1 | 12/2001 | Hyppölä | 128/203.15 |
| 6,478,196 | B2 | 11/2002 | Fuchs | 222/321.6 |
| 6,521,223 | B1 | 2/2003 | Calias et al. | |
| 6,695,220 | B2 | 2/2004 | Vollmer | 239/8 |
| 6,799,571 | B1 | 10/2004 | Hughes et al. | 128/203.12 |
| 7,131,558 | B2 * | 11/2006 | de la Guardia | 222/209 |
| 7,222,803 | B2 * | 5/2007 | Bolton | 239/326 |
| 7,303,759 | B2 | 12/2007 | Mershon | |
| 2002/0011530 | A1 | 1/2002 | Fuchs | 239/333 |
| 2002/0177534 | A1 | 11/2002 | Paul | 510/130 |
| 2004/0082907 | A1 | 4/2004 | James | |

FOREIGN PATENT DOCUMENTS

| | | |
|---|---|---|
| EP | 0 407 276 A3 | 1/1991 |
| EP | 1 116 522 B1 | 11/2003 |
| GB | 2151244 | 7/1985 |
| WO | WO 86/00079 | 1/1986 |
| WO | WO 86/00912 | 2/1986 |
| WO | WO 01/82863 A2 | 11/2001 |

OTHER PUBLICATIONS

Danishefsky et al., 1971, Carbohydrate Res., vol. 16, pp. 199-205.
Laurent et al., 1964, Acta Chem. Scand., vol. 18, p. 274.
Sparer er al., Chap. 6, pp. 107-119, in T.J. Roseman et al., Controlled Release Delivery Systems, Marcel Dekker, Inc., New York.

* cited by examiner

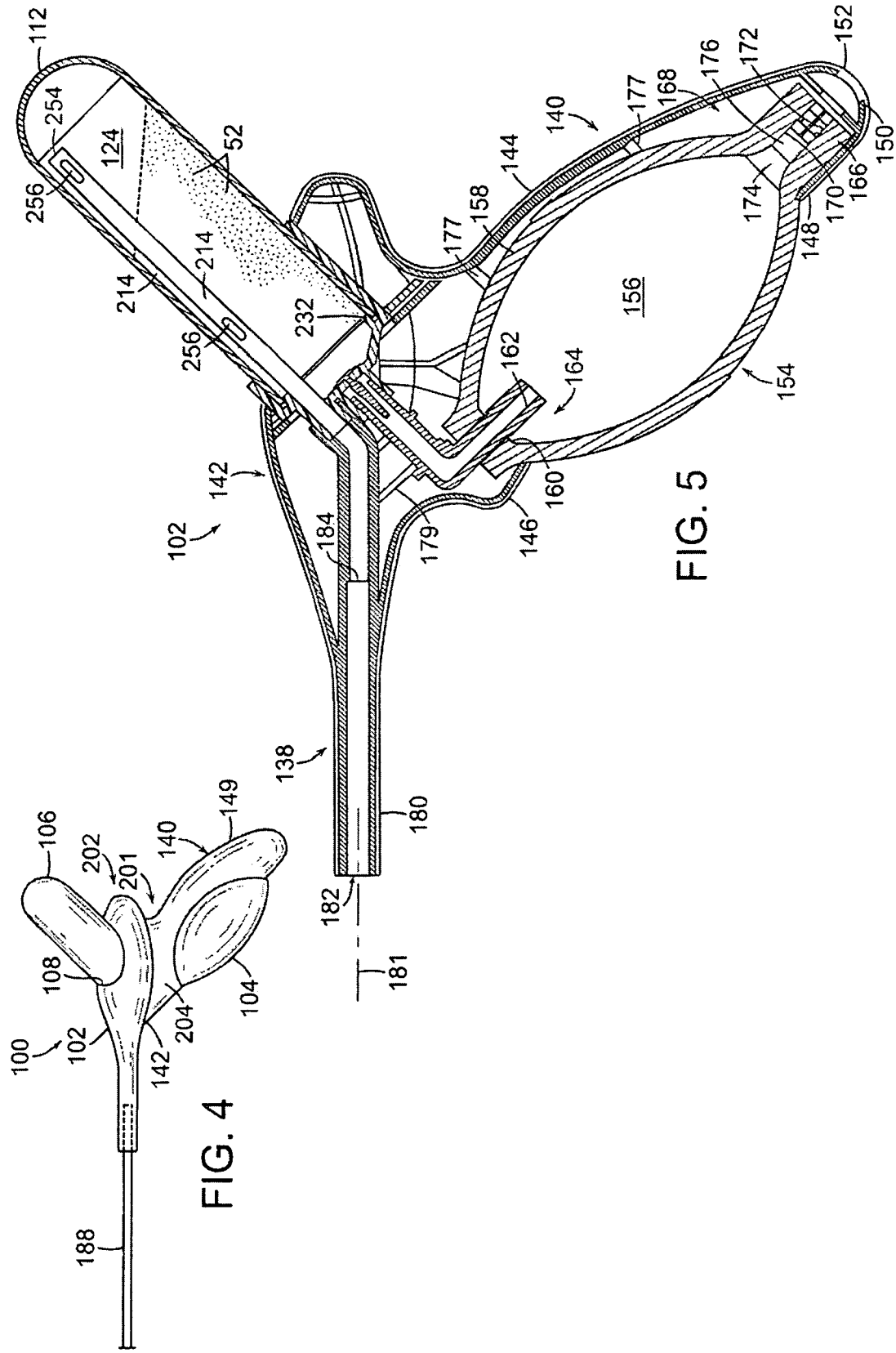

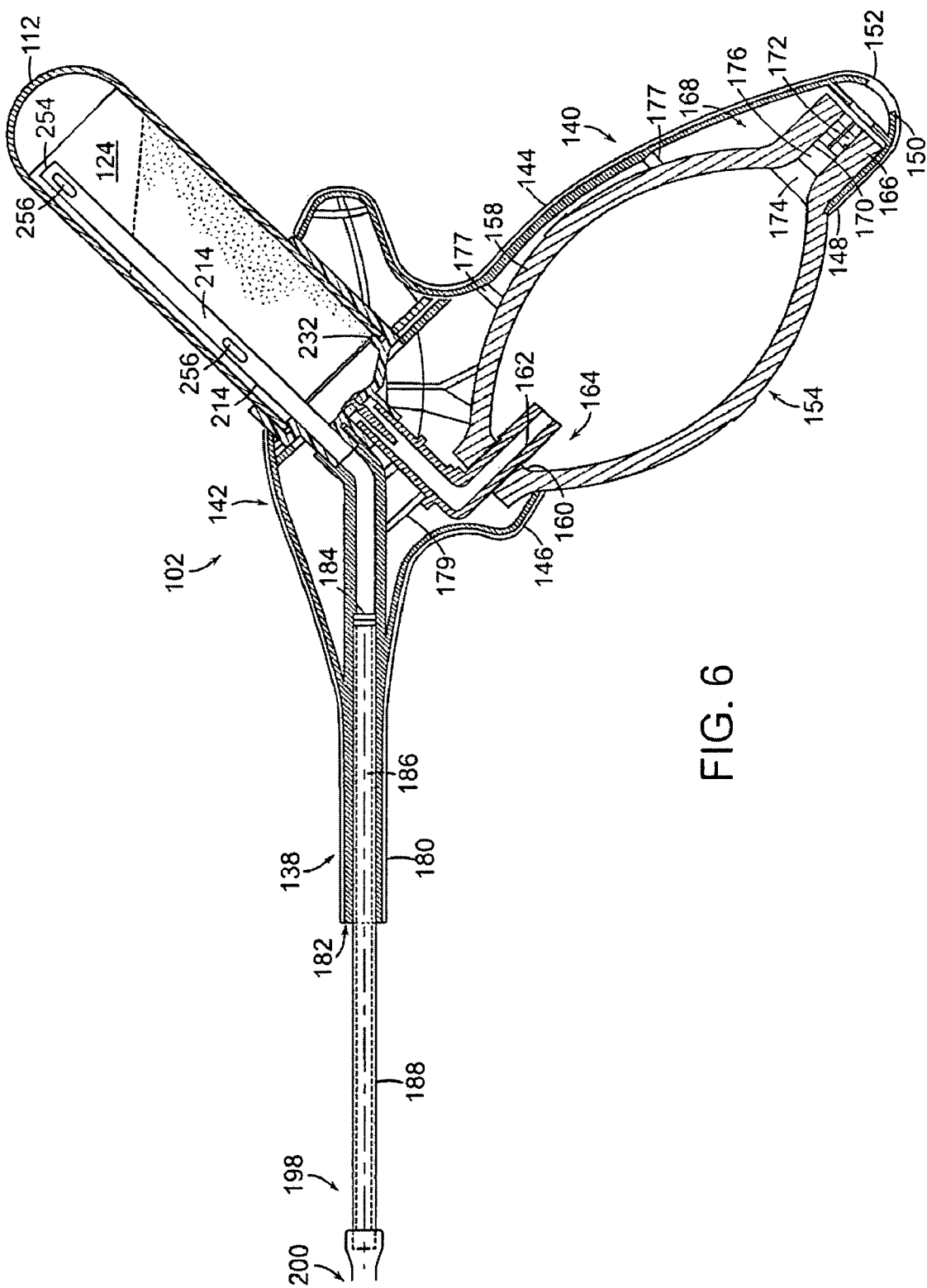

POWDER DELIVERY DEVICE

This application is a continuation-in-part of U.S. Provisional Patent Application Ser. No. 60/554,009, filed 17 Mar. 2004 for "Anti-Adhesion Spraying" by J. Jeffrey Kablik; Keith E. Greenwalt and M. Jude Colt (the same inventors as of this application) as assignors to Genzyme Corporation, the entire content of which is expressly incorporated herein by reference.

BACKGROUND

1. Field of the Invention

The present invention generally relates to devices for the delivery of powdered materials from a storage reservoir to a target surface area in the form of an aerosolized powder spray. More specifically, the present invention relates to a convenient, self-contained, single-hand-held, single-hand-operated device for both aerosolizing and delivering powdered materials in the form of a spray so as to substantially evenly coat a target surface area with a desired and/or predetermined quantity of powdered material. Still more particularly, the present invention relates to a device for the application of medicinal materials in powder spray form to selected target surface areas such as areas located in and/or around open or "closed" laparoscopic surgical fields of substantially any size and degree of visibility.

2. Summary of the Prior Art

Most materials may be easily and advantageously manufactured, distributed and stored in powder form. This is significant because the powder form of various materials and/or compositions often can be premixed for future use in a manner such that the resulting mixture evidences minimal component separation problems during storage. Further, the size of the constituent elements (i.e., particles) of a powder mixture can be controlled so as to insure that a substantially homogeneous distribution of a desired concentration of each of those constituent elements is achieved when the powder mixture is spread over a specified area. Indeed, it often has been found to be possible to achieve a more homogeneous material distribution on, and more complete material coverage of, a target surface area when the applied materials are in powder form than when those materials are disbursed in the form of liquid droplets entrained in a propellant stream as in a conventional aerosol spray.

Powder delivery devices of numerous forms are known generally in the art. These known devices range from the simple to the complex, and have found use for a broad multiplicity of purposes ranging from the application of industrial coatings to work-pieces, to the application of insecticides both indoors and outdoors, to the marking of boundaries or particularly determined locations, to the delivery of medicinal materials to patients both topically and internally, among very many others.

Perhaps the simplest powder delivery device known is the simple shaker. Shakers typically take the form of containers with holes in their tops that are inverted and shaken to cause a material in powder form stored within the container to be selectively discharged from the container through the holes. For example, shakers are often used in the topical application of powders, such as in the topical application of talcum powder to the surface of the skin. The control of the flow of the powder through the holes of a shaker, however, is not accurate, and the resulting coverage of the desired target surface area is not usually uniform. This is because in use the agglomerated powder in the container is broken up non-uniformly by the abrupt stoppages of the movement of the container at the extremes of the up and down limits of the applied shaking motion, and also because the flow of the non-uniformly broken up powdered material through the holes cannot be accurately controlled.

Another well-known powder delivery device is the so-called "atomizer" often used in the treatment of conditions such as asthma. This type of powder delivery device is easily used, often by untrained individuals, and also typically includes provision for the secure storage of a powdered material to be delivered as well as provision for the generation of a propellant stream within the device, as will be discussed further below.

Still more complex powder delivery devices also are known including, for example, structures designed for the sequential delivery of measured unit doses of powdered materials from the device. Known powder delivery devices of the latter type commonly include at least one internal powder metering chamber from which only single, pre-measured volumes of a powdered material constituting predetermined dosage quantities thereof can be expelled at any one time. These devices also often include provision for the automatic refilling of the powder-metering chamber subsequent to each discharge of the content thereof in use.

In most medical applications, it has been found to be desirable for medicinal powdered materials to be delivered to their target areas in the form of a "soft cloud" in which the particles constituting the powder remain in a visibly separated relationship relative to one another as they travel from the delivery device to the target area. This avoids the infliction of trauma to bodily tissue in the area to be coated by the powder material. However, despite their high cost and the often disadvantageous (or damaging) force of their output sprays, homogeneous spray delivery devices such as closed aerosol cans containing a supply of powdered material and a gas under pressure for discharging a concentrated aerosolized powder stream, are often used for medicinal powdered material delivery. This is primarily because users are generally familiar and comfortable with the operation of common aerosol cans. In addition, the typically single-hand-held, single-hand-operated nature of standard aerosol cans, as well as the substantial reliability of the directionality and homogeneity of the output sprays achieved by standard aerosol cans, are contributing factors to their use as powdered material spray devices despite the drawbacks mentioned above.

As briefly alluded to above, powder materials stored in a container tend to agglomerate into a cohesive mass. This is true whether the container constitutes a part of the powder delivery device or is external to the powder delivery device. Consequently, delivery devices for powdered materials require not only that the powdered material be conveyed in a propellant stream to the target site, but also that preliminarily to its discharge from its storage container (reservoir), the powdered material being transferred to the target site be separated from the remainder of the agglomerated mass of stored powder in the container/reservoir and aerosolized.

The result of the foregoing steps is the creation of a desired powder concentration within a propellant at, or substantially immediately prior to, its discharge from the device toward the target surface area. To accomplish the latter objectives, numerous devices have been suggested in the art for the control of the aerosolization of a powdered material stored in a container as well as for the discharge of an aerosolized powder from a container in a manner calculated to achieve a desired, substantially homogeneous coating of a target surface area.

An example of a device of the latter type is known in connection with the delivery of asthma medication in powdered form. In this case, the interior of the container/reservoir/dosage chamber includes provision both for aerosolizing the stored powder as well as for the projection of the aerosolized powder into the lungs and sinus cavities of the patient so as to substantially homogeneously coat, and thereby treat, the internal bodily tissue making up the patient's respiratory system. Devices of this type, often referred to as "inhalers" or "atomizers", typically include a gaseous material under artificially created pressure such as an aerosol can or an external pressurized propellant supply that is released into (and from) a powder storage reservoir.

Alternatively, however, a mechanical pump such as a plunger mounted adjacent to a powder containing reservoir also often is used to create a suitable propellant stream. In the latter case, the user forces a gaseous material (typically air) into the reservoir under pressure by the depression of the plunger or a similar mechanical manipulation of the device in a manner that causes a flow of propellant (typically air) to aerosolize at least a predetermined minimum quantity of the stored powder in the reservoir and to discharge substantially all of the so aerosolized powder to a spray head and thence to the surfaces of the patient's respiratory system that are to be treated.

Asthma "inhalers" typically are small devices that fit well in a patient's pocket or purse. Further, they generally are easy to use as well as being single-hand-held and single-hand-operated devices. Nevertheless, the user typically places the discharge orifice of the "inhaler" into his mouth prior to depressing the plunger or otherwise injecting a pressurized gas into the container/reservoir. Hence, without its interaction with the patient's mouth, an "inhaler" type device does not provide an easily manipulated device that is suitable for use in the controlled and accurate delivery of aerosolized powders to target surfaces generally, and particularly is not suited to the delivery of powdered materials for reliable target surface coating into small area surgical sites that are often not readily visible (for example, laparoscopic surgical sites).

The well-known, simple so-called "puffer", on the other hand, is a device wherein the powder reservoir commonly constitutes, in its simplest form, a container with inwardly deformable sides having both an outlet port and a one-way inlet valve. In this form of powdered material spray device, a quick and forceful inward deformation of the container walls causes a portion of a quantity of powder stored within the container to be aerosolized and thereafter discharged in the form of a "puff" (as in a "puff of smoke") from the outlet port (i.e., to be separated from the agglomerated stored powder mass and entrained in the gas being discharged from the interior of the container by the quick and forceful inward collapse of its side walls).

Thereafter, the collapsing force on the container walls is released, and the resilient nature of the material of the container tends to cause the container to resume its original shape. As this shape resumption occurs, the partial vacuum created within the container as the walls of the container attempt to expand outwardly to resume their original shape is released by allowing air to enter the container through the one-way valve. Hence, the reversal of the deformation of the container is easily completed. This type of "puffer", although subject to clogging at its inlet and outlet in a manner similar to the simple shaker, nevertheless has been found to work reasonably well for topical applications of aerosolized powders such as for example to the surface of the skin or within large so-called "open" surgical sites wherein the target surfaces to be coated with the powdered material are both visible and readily accessible. However, in those cases in which the surface to be coated is not visible or otherwise readily accessible, the simple "puffer" and similar powdered material delivery device designs have been found not to be efficiently or satisfactorily workable.

To deal with the foregoing problems inherent in simple powdered material delivery devices, systems have been developed in which propellants are used in connection with extended conduits (i.e., cannulas) to project powder sprays generally, as well as particularly into relatively inaccessible areas of "open" surgical sites, or indeed into relatively inaccessible and invisible locations, such as internal laproscpic surgical sites. These aerosol spray based systems have the benefit of at least sometimes being single-hand-operable (i.e., in those cases in which one hand of the operator is not required to hold and operate the propellant source while his other hand controls the direction of the spray).

An example of one such system, generally and illustratively shown in FIG. 1, includes a conventional aerosol propellant can 2 having the exit portal of its aerosol release valve 4 extended via a cannula or other form of conduit 6 so as to allow an output of aerosolized powdered material to be more accurately directed and/or concentrated.

Devices/systems of this type, while sometimes useful for the spraying of topical powdered materials in generally open settings, have proven to be unsatisfactory when the target surfaces are located in confined volumes in which a so-called "soft cloud" spray is desired and/or necessary. Accordingly, particularly for the spraying of medicinal powders so as to homogeneously coat small (and/or confined) internal operative sites without the infliction of damaging trauma to the target tissue conventional aerosol propellant can type devices are contra-indicated. This is because factors such as (i) air leakage at the can/valve interface and/or point of attachment of the valve to the spray directing extension member, (ii) the inability satisfactorily to control the velocity of high-pressure aerosolized powder sprays generated by typical aerosol can valves, and (iii) the well known inability of typical aerosol cans to reliably discharge homogeneous sprays when spatially oriented in inverted positions with their release valves disposed below the horizontal, among other factors, all significantly tend to reduce both the reliability and the medical functionality of the conventional aerosol can form of powder sprayer.

The system currently most favored in the art for surgical/laparoscopic medicinal powder spraying utilizes the so-called "Wolf" sprayer as generally and illustratively depicted in FIGS. 2 and 3. This system, generally indicated at 8, includes a propellant source such as a source of pressurized gas (represented by a closed can 18, but permissibly including connection to an external compressor, for example via a wall fitting provided in an operating room) provided with the capability of discharging a pressurized gas in the form of discrete pulses, see element 12 (FIG. 2), or alternatively, a hand pump such as that generally indicated at 10 (FIG. 3). The hand pump 10 ideally is operated by the exertion of quick, forceful pressure against a deformable portion 14 so as to expel the air content of the pump through a discharge tube 16 in the form of a gas pulse.

The metered pulse source of pressurized gas 12, on the other hand, is more complex. In particular, it generally includes the propellant source 18 connected to a valve 20 by a conduit 22. Further, the valve 20 is constructed so as to periodically alternately open and close thereby permitting the controlled discharge of uniform gas pulses into a discharge tube 24. More specifically, a metered quantity (pulse) of propellant under controlled maximum pressure is introduced into the conduit 22 for release by the valve 20 in the form of a gas pulse of predetermined size and pressure similar to that achievable with the hand pump 10 shown in FIG. 2. Of course, the structure depicted in FIG. 2 is superior to that of FIG. 3 in terms of its control of the size and pressure of the pulse and hence also in terms of the powder dosage that will eventually be carried to the target surface area of the patient. On the other hand, however, the structure depicted in FIG. 3 provides greater versatility than that of FIG. 2 due to the less complex nature of the pulse creation means, and the fact that it is not tied to an expensive and/or fixed pressurized gas source.

As will appear more fully below, however, both of these propellant sources are cumbersome, expensive and at least somewhat complex. Further, the systems of which those propellant sources form a part are further limited by the required substantially vertical spatial disposition of their Wolf-type powder reservoir in a manner that renders single-hand-held operation of the device substantially impractical, if not impossible.

In addition, it is to be recognized that particularly in the case of delicate surgical procedures involving delicate tissue structures, there is a tendency for a user to be at least somewhat tentative in the application of the aerosolized powder to the target surface. Accordingly, it can be expected that the deflation forces sequentially applied by such a user to the flexible portion 14 of the pump 10 often will be such that the flexible portion 14 is not fully deflated by each applied force imparted to it by the user. In devices/systems such as that depicted in FIG. 3, this often results in the unsatisfactory operation of the remainder of the device.

Therefore, it will be understood by those skilled in the art that in the devices depicted in FIGS. 2 and 3 the respective conduits 16, 24 input gas pulses such as those discussed above into an aerosolizing device (commonly designated as a so-called "Wolf Sprayer") shown generally at 26. This aerosolizing device 26 includes a reservoir portion 28 having the general form of a test tube (i.e., an elongate substantially cylindrical portion 30 having a generally hemispherical closed end 32), and a cover member generally indicated at 34.

The cover member 34 defines an input conduit 36 that extends from a fitting 38 outside of the cover member through the cover to an elongate section 40 that extends almost to the closed end 32 of the reservoir portion generally parallel to the longitudinal axis of the reservoir. The cover member 34 also defines an output conduit 42 that extends from a fitting 44 through the cover member to a section 46 substantially shorter than the elongate section 40 of the conduit 36 that also extends into the reservoir substantially parallel to the longitudinal axis of the reservoir. Of course, it will be understood that the cover member 34 is generally substantially more complex than is illustratively shown in FIGS. 2 and 3. For example, a lower portion of the cover is commonly screwed or otherwise secured in removable sealed relation to a top portion thereof. This allows the reservoir to be slid through the lower portion such that an outwardly extending flange at its open end (not specifically shown) engages an inwardly extending flange at the bottom of the lower cover portion (also not specifically shown). Thus, the reservoir may be filled, refilled and/or replaced only by the cumbersome and inconvenient disassembly of the cover and the removal of the reservoir therefrom. In addition, these complexities in the construction of the cover also create a potential for gas leakage at the connection of the lower and top portions of the cover member. Further, they introduce serious problems in the accomplishment of the satisfactory sterilization the components of the device and its content prior to their use in and/or near open surgical fields.

Finally, a flexible or rigid conduit 48 extends from the output fitting 44 of the cap member 34 to a spray head generally indicated at 50.

With this system, as generally indicated by the arrows depicted within the reservoir 28, a gas pulse from the propellant source is introduced into a quantity of powder generally indicated at 52 stored in the portion of the reservoir 28 adjacent to its closed end through the input conduit 36 (assuming that the open end of the elongate section 40 of the input conduit 36 has not been clogged by agglomerated powdered material located in the reservoir at the time of its original insertion into the reservoir 28 during the assembly of the cap to the reservoir as generally discussed above).

The gas pulse mixes with the powder stored in the reservoir in a sort of swirling motion adjacent to the closed end 32 of the reservoir 28 (see representative arrows in the reservoir) thereby aerosolizing at least some of the stored powder into the open head space located between the top of the stored powder mass and the cover (i.e., to entrain some of the powdered material in the pressurized gas located in the open head space between the surface of the agglomerated powdered material in the bottom of the reservoir and the open top thereof that is sealed by the cover member) in the form of a cloud of separate powdered material particles. Concurrently, the increased pressure introduced into the reservoir by the input propellant pulse forces at least part (usually a major portion) of the aerosolized powder in the head space of the reservoir out of the reservoir and through the cover member via the open end of the output conduit 42 located within the head space of the reservoir, and thence to the spray head 50.

Accordingly, it will be understood that the tentative operation of the hand pump mentioned above often is insufficient to generate a gas pulse of adequate duration and pressure to cause the operation of the device just discussed to occur, or if that operation does occur, to cause it to occur in a satisfactory manner. Similarly, while less likely, the partial release of a pressurized gas pulse in the structure depicted in FIG. 2 due to the tentative actuation of the release valve also can cause insufficient aerosolization and discharge of powdered material.

These results can be very problematic because, as mentioned briefly above, there is a natural tendency for individuals performing close, delicate and complex tasks to do so utilizing small movements so as to maintain better control over the effects of their actions. Consequently, it will be understood that the preferred manner of operating the currently preferred devices is counterintuitive to this natural tendency of operators such as those in the surgical field with results that are at best less than optimum quantities of powdered material spray impinging upon the target surface area.

Furthermore, also as briefly mentioned above, the currently preferred powdered material delivery systems depicted in FIGS. 2 and 3 are cumbersome, expensive and essentially impossible to operate with one hand regardless of whether a pump 10 or a metered propellant source 12, is used. Instead, it has been found that the propellant source typically must be operated with one hand while the other hand of the operator controls the spray head so as to direct the output powdered material spray to the desired target surface areas.

Still further, also as briefly mentioned above, it will be understood that in the currently preferred devices, the longitudinal axis of the reservoir must be maintained in a substantially vertical spatial position in order to ensure that the powder stored therein is aerosolized in the desired manner. As is readily apparent from the drawings (FIGS. 2 and 3), the further the reservoir is tilted from the vertical, the smaller the affect the input propellant pulses will have on the stored, agglomerated powder, particularly as the quantity of powdered material in the reservoir is used up (i.e., discharged from the sprayer). This is most significantly the case when the top of the reservoir is tilted to the right as depicted in FIGS. 2 and 3 because in that event the surface of the powder stored in the reservoir tends to tilt at an angle to the longitudinal axis of the reservoir rather than being located substantially normal thereto. This results in the surface of the stored powdered material approaching the outlet of the aerosolizing pulses into the reservoir thereby reducing the mixing action of input propellant pulses within the agglomerated powder stored in the reservoir (and indeed, possibly clogging the opening of the output conduit located within the reservoir).

Hence, the further from the vertical the longitudinal axis of the reservoir in a so-called "Wolf" sprayer is tilted, the smaller the control that can be exerted upon the quantity of powder aerosolized by each propellant pulse (assuming no clogging and the adequacy of the pressure contained in each pulse). In other words, the tilting of the reservoir skews the disposition of the powder stored in the reservoir in a manner that changes the quantity of the stored powder directly impacted by the input propellant pulses within the body of the stored powder (see arrows depicting propellant flow within the reservoir shown in FIGS. 2 and 3). Therefore, tilting of the reservoir reduces the control of the powder dose aerosolized by each pulse because less powder is influenced by the full impact of the propellant pulse thereby placing significant constraints upon the manner in which the system is required to be used.

In addition, since the cross-section of the output conduit is limited, the quantity of aerosolized powder that can be delivered by each propellant pulse also is limited. Still further, it has been found to be difficult to ensure that all of the powder stored in the reservoir can be delivered satisfactorily by the devices generally depicted in FIGS. 2 and 3. This adversely affects the efficiency of powdered material use. Consequently, inefficient overfilling, refilling and/or a switch to a new device prior to the use of all of the stored powder in a particular reservoir all have been found to be necessary operational drawbacks encountered in the use of the currently preferred system for the delivery of medicinal powders to and in the vicinity of surgical sites.

In summary, therefore, the currently preferred concept for the generation and spray of powdered materials is cumbersome in structure and typically requires two-handed operation by the user thereby preventing the user from performing other tasks with one of his hands. Also, the various components of the device are not easily sterilized, yet they are designed for reuse rather than being single-use disposable devices. These are important disadvantages, particularly in a surgical setting in which the available space for each surgeon or technician to perform is limited yet the efficiency with which all surgical tasks can be performed within the available area is significant.

SUMMARY OF THE INVENTION

Accordingly, it is an object of the present invention to provide a self contained, single-hand-held, single-hand-operated powder delivery device that also may be pre-sterilized and distributed as a single-use device.

It also is an object of the present invention to provide a single-hand-held, single-hand-operated, powder delivery device that is efficiently and satisfactorily operable when a powdered material containing reservoir portion thereof is inverted and/or tilted relative to the conventional open topped vertical configuration.

Further, it is an object of the present invention to provide a powder delivery device in which clogging by the powdered material is minimized at the input to, and the output from, a powdered material containing reservoir both during the assembly of the components of the device and during the operation thereof.

Still further, it is an object of the present invention to provide a powder delivery device in which output quantities of aerosolized powder are easily and accurately controllable, and if desired quantified.

Another object of the present invention is to provide a powder delivery device in which the size of the reservoir and the deliverable portion of the powder contained in the reservoir may be selected such that a predetermined quantity of powdered material can be dispensed by the device onto a target surface without overfilling/refilling of the reservoir and/or replacement of the reservoir and/or the substitution of another powdered material delivery device during the course of a particular surgical procedure, or some other defined usage context.

A further object of the present invention is to provide a powder delivery device including interchangeable, pre-sterilized, disposable, powdered material reservoirs and wherein when/if a change of one reservoir for another is required for any reason that change may be accomplished easily and securely without adverse impact upon the continued delivery of powdered material to the desired target surface area.

Still further, it is an object of the present invention to optimize the spray pattern and angle of delivery of aerosolized powdered material from a powder delivery device to a desired target area in a manner that ensures adequate and substantially homogeneous coverage of the target area by the powdered material.

Still another object of the present invention is to provide a powder delivery device that is adjustable in configuration such that it is useable as both a topical applicator and as a means for the delivery of aerosolized powder into small and otherwise inaccessible (and/or invisible) locations.

A still further object of the present invention is to provide a powder delivery device wherein the duration and pressure level of each applied propellant pulse may vary over a wide range of values above a predetermined minimum value without a failure in powdered material delivery to a target surface area.

These and other objectives of the present invention are accomplished in a preferred embodiment by the provision of a self-contained, single-hand-held, single-hand-operated, powder delivery device that is particularly useful in, among other contexts, the delivery of medicinal powders useful in the creation of adhesion barriers to target surface areas in and around so-called "open" and/or "closed" surgical sites.

The powdered material delivery device (or system) in a preferred embodiment of the present invention generally includes at least one reservoir for storing a quantity of powdered material to be delivered and a generally pistol-shaped housing including a receptacle for receiving and removeably holding a selected one of the at least one powdered material reservoir.

More particularly, the preferred embodiment of the present invention consolidates a function of supplying a propellant to the interior of the reservoir, a function of aerosolizing at least some of an agglomerated mass of powdered material stored in the reservoir, and a function of delivering an aerosolized powder spray from the reservoir to a target surface area into a convenient, single-hand-held, single-hand-operated device. Further, in a preferred embodiment of the present invention, the structure of the housing is designed such that (i) clogging in the apparatus is reduced in comparison to other powdered material spray devices, (ii) the delivery of bulk powders having particle sizes of at least between about 100 and 425 micrometers in diameter may be achieved, (iii) the pattern and coverage area achievable by the output spray from the device is optimized, and (iv) dosage levels (i.e., output per input propellant pulse as described in more detail below) may be accurately controlled in the event that such control is important and/or required.

In addition, a preferred embodiment of the device according to the present invention permits the longitudinal axis of the reservoir when mounted in the receptacle portion of the housing to be fixed at upwardly slanted angle of about 45° relative to a horizontal spatial orientation of the housing. This is to be contrasted with the limited, essentially vertically downward, spatial orientation to the horizontal required by previously preferred prior devices as discussed above.

As will appear more fully below, this configuration of the integrated housing and reservoir portions of the device in the preferred embodiment of the invention allows the integrally assembled device to be essentially freely manipulated by an operator. Specifically, the longitudinal axis along which delivery of the output spray of powdered material from a preferred form of the device is centered (prior to any subsequent deflection) may vary within a range as large as from about 0° and to about 90°, and more particularly between about 20° and about 70°, below a horizontal spatial orientation of the housing. In other words, it is contemplated that the pistol-like housing of the preferred embodiment may be grasped by its handle portion and manipulated such that the open end of its barrel portion is pointed downwardly at the usual angles at which a surgeon would desire to direct a medicinal powder onto a target surface associated with a surgical site from above the surgical site (or for that matter at which most users would desire to direct a powder spray onto a target surface from above the target surface) without adverse operational impact upon the powder aerosolizing and/or delivery functions of the device.

Further, the preferred embodiment of the present invention includes the capability of delivering substantially all of the powder in a powdered material-containing reservoir prior to the necessity of refilling the reservoir or of switching the reservoir for an interchangeable substitute reservoir filled with powdered material, or the need to adopt the use of a totally distinct powder delivery device.

Each and all of the foregoing features represent important improvements over the current state of the art discussed generally above. More specifically, as will be appear further below with regard to a particularly preferred embodiment of the invention, the powder delivery device of the present invention is self-contained, single-hand-held, single-hand-operated, convenient and easy to use for both topical and limited area powder delivery without the functional limitations of the prior art.

In particular, the preferred embodiment of the present invention described herein generally includes a powdered material reservoir designed to securely, yet removably, engage a receptacle of a housing. Generally speaking, the powdered material reservoir is an elongate, hollow member having a closed, generally hemispherical end and an open end similar to that discussed above with regard to the prior art. Also, the outer surface of the reservoir adjacent to its open end is provided with engagement means for interaction with the receptacle of the housing to securely, sealingly, yet easily removably, maintain the reservoir in securely attached relation to the receptacle of the housing in the desired configuration.

In a particularly preferred form of the invention, the engagement means securing the reservoir to the receptacle of the housing includes a pair of J-shaped or L-shaped slots disposed diagonally opposite to one another in the outer surface of the reservoir. More particularly, the longer leg of each of the slots (that extend radially into, but not through, the side walls of the reservoir) open into the open end of the reservoir and extend along the outer surface of the reservoir substantially parallel to its longitudinal axis. The shorter legs of these slots, on the other hand, extend generally circumferentially along the surface of the reservoir substantially normal to the closed end of the longer leg portion of their respective slot. Thus, as will become further apparent below, the slots in the outer surface of the reservoir may be engaged by corresponding projections associated with the receptacle of the housing so as to maintain the releasable, sealed attachment and orientation of the reservoir relative to the receptacle.

In addition, the J-shaped or L-shaped slots may be used to engage inwardly extending projections from a cover member having an open end, cylindrical walls and a closed end so as to securely maintain a preselected quantity of powdered material in the reservoir during sterilization and storage prior to the attachment of the reservoir to the receptacle portion of the housing. Accordingly, it is contemplated that the device may include one or a plurality of interchangeable reservoirs, and that each reservoir may be pre-filled and pre-sterilized for removeable attachment to the receptacle of the housing as necessary or desired.

The housing in the preferred embodiment also is contemplated to be a pre-sterilizeable and/or a disposable unit. Generally speaking, the housing is a substantially pistol-shaped structure including a hollow barrel portion, a handle portion disposed at a downward, rearwardly extending angle relative to the longitudinal axis of the barrel portion, and a connecting portion located between and joining the handle and barrel portions. In addition, the connecting portion defines the receptacle, mentioned briefly above, that is designed to receive and hold the open end of the reservoir in sealed relation to the housing. In particular, the receptacle is constructed in such a way that when a reservoir is engaged therewith, the longitudinal axis of the reservoir inclines rearwardly and upwardly relative to the longitudinal axis of the barrel portion at an angle of about 45° in substantially the same plane in which the handle portion extends rearwardly at a downward angle from the connecting portion.

The handle portion defines a central hollow cavity, an inlet selectively connecting the hollow cavity to the surrounding atmosphere at its outer end and an outlet connecting the hollow cavity to the connecting portion. The side walls of the hollow cavity are constructed so as to be readily and easily grasped by a hand of a user and also such that the hollow cavity can be selectively collapsed, usually quickly and forcefully, by a user's hand in a manner that forces the majority of the content of the hollow cavity through its outlet. The hollow cavity of the handle collapsed in the foregoing manner is contemplated to resume its non-collapsed state upon the release of the collapsing force of the user's hand by virtue of the resilient nature of the material from which it is made and input received through its inlet (i.e., by air or another propellant entering the collapsed handle via the one-way inlet valve or the like at its outer end).

The barrel portion of the housing is an elongate hollow shaft centered on a longitudinal axis. The shaft is open to the atmosphere at a free end thereof and opens into the connecting portion at its other end. Further, the interior cross-section of the barrel is sized to receive a cannula in snug fitting relation therein in selected situations as discussed further below.

Thus, in one version of the preferred embodiment of the present invention, a cannula extends into the open end of the barrel portion of the housing. In this embodiment, the barrel portion defines a reduced diameter portion adjacent to the connecting portion so as to form an annular stop against which the end of the cannula inserted into open end of the barrel abuts in the fully assembled condition. In the latter configuration, engagement means may be provided on the outer surface of the cannula adjacent to its inserted end and on the portion of the barrel shaft adjacent to the stop that interact with one another to insure the secure disposition of the cannula in the shaft defined by the barrel portion. For example, these engagement means may take the form of an encircling groove adjacent the inserted end of the cannula and one or more radially inwardly extending projections from the interior of the shaft of the barrel portion that engage the groove in the cannula upon its full insertion into the barrel portion of the housing. Otherwise, the barrel portion constitutes an elongate shaft attached to the connecting portion for directing the output powdered material spray from the device.

The use of the cannula allows the output of the device to be placed directly into small, relatively inaccessible areas such as laparoscopic surgical sites. In those cases, the available area for movement of the device relative to the surface to be coated by the powder typically is small. Further, there also may be a need to orient the device in space such that the longitudinal axis of the barrel does not remain straight in use (i.e. there may be a need in some situations to bend the discharge opening of the cannula relative to its primary longitudinal axis, for example by pulling on an embedded guide wire in the wall of the cannula). In the latter case, direct visualization of the surface(s) to be coated with the powder by the user may be either difficult or impossible.

To compensate for these difficulties, in addition to the features discussed above, the present invention contemplates that the outer end portion of the cannula may be provided with a diffuser either built into the cannula or attached thereto at its outer open end so as to optimize the spray pattern of the emitted aerosolized powder. Of course, a similar diffuser also may be provided at the outlet from the barrel regardless of whether or not a cannula is used so as to optimize the spray pattern in all cases.

In a particularly preferred form, the diffuser geometry is such that the interior diameter of a cross-section of the cannula or fitting attached to the outer open end thereof smoothly narrows to a predetermined extent and thereafter expands back to its original diameter over a predetermined length. In one specifically preferred embodiment, the outer end portion of a 0.18 inch diameter cannula narrows to a diameter of about 0.15 inches over a cannula length of about 0.35 inches. It will be understood by those skilled in the art, however, that the optimal design for diffusion of the aerosolized powder being discharged from the device may vary according to the particular size of the cannula used and the type and size of the powder particles entrained in the aerosolized powder flow among other variables.

The lower rear part of the connecting portion of the housing defines a grip portion adjacent to the handle portion that is contemplated to include an outer contour designed to receive the portion of the operator's hand joining the operator's thumb and forefinger while the lower side portions thereof are contoured to receive the operator's thumb and forefinger, respectively. Hence, the housing is easily grasped and held by the operator in a manner analogous to the conventional gripping of the handle of a pistol.

Finally, the connecting portion includes the receptacle, conduit means connecting the output of the handle portion to an input to the receptacle, an internal output shaft connected to the shaft of the barrel portion, and a hollow, elongate output member extending from the internal output shaft within the connecting portion through an output opening in the receptacle and projecting outwardly from the receptacle a distance substantially equal to the longitudinal length of the reservoir between the open and hemispherical ends thereof.

The receptacle basically constitutes a cavity extending into the outer surface of the connecting portion that includes two parts. The first of these parts includes an outer cavity having a substantially circular cross-section extending into the surface of the connecting portion. In the preferred embodiment shown in the drawings, the portions of the sidewall of this circular cavity located closest to the rear of the housing have a greater axial length than the opposing portions thereof due to the surface contour of the connecting portion. Accordingly, when a reservoir is disposed in the receptacle, a larger portion of the axial length of the reservoir is supported from below and behind it than from above and forward of it. In addition, the base of the first portion of the receptacle lies in a plane substantially normal its sidewalls.

In particular, at the base of the first portion of the receptacle spaced inwardly a distance slightly less that the interior diameter of the open end of the reservoir is a short inner wall having an inner surface that slants inwardly toward the longitudinal axis of the circular cavity from its bottom edge to its top edge. This short wall acts to define with the outer wall of the first part of the receptacle and its base a circular channel adjacent to the base of the first portion of the receptacle that is adapted to receive the open end of the reservoir.

More specifically, inwardly extending diagonally opposed projections are located on the outer wall of the receptacle. The interaction of these elements with the reservoir is such that as the open end of the reservoir is inserted into the receptacle, the inwardly extending projections engage the slots in the outer surface of the reservoir and the inner diameter of the open end of the reservoir is brought into engagement with the inner slanted surface of the short wall of the channel. Then, as a result of pushing the reservoir axially into the receptacle until it can be twisted about its longitudinal axis such that the projections from the side wall enter the shorter length legs of the J-shaped or L-shaped slots in the exterior of the reservoir, the inner diameter of the reservoir is forced and releasably locked against the inner slanted wall of the channel. Hence, the open end of the reservoir is disposed in the channel at the base of the first portion of the receptacle in sealed engagement therewith.

The remainder of the receptacle includes a cavity having a flat bottom portion connected to the base of the first portion by outwardly curved sidewalls. This second part of the receptacle extends into the connecting portion along the longitudinal axis of the first part below the level of the base of the channel. An opening in the flat bottom portion of this cavity constitutes the inlet to the receptacle that is connected to the handle portion of the device by appropriate conduit means located within the connecting portion. In addition, a one-way valve, in the preferred embodiment a so-called "mushroom" valve, is disposed in the conduit connecting the handle portion to the inlet of the receptacle to the handle. This valve has a large head that overlaps the entire circumference of the inlet opening in the bottom of the receptacle and a stem portion residing in and interacting with the conduit such that the stem/head combination is allowed to move outwardly a small distance in response to output propellant pulses from the handle whereby the input gas pulses flow into the receptacle around the base of the large head. Otherwise, when no input pulse is flowing through the conduit, the enlarged head of the valve closes down over the inlet opening in the bottom of the receptacle preventing a backflow of powdered material into the connecting conduit or handle portion.

Above the flat-bottomed portion of the inner cavity of the receptacle, the hollow elongate output member extends through the curved wall portion of the second part of the receptacle substantially parallel to the longitudinal axis of the circular cavity first part of the receptacle. As noted above, one open end of this elongate hollow member communicates with the end of the internal channel defined by the connecting portion that opens at its other end into the hollow barrel portion. The other open end of the elongate, hollow output member resides at a distance outwardly from the receptacle such that when a reservoir is mounted in the receptacle that other open end resides substantially adjacent to the closed hemispherical end of the reservoir and the elongate member is disposed substantially along the sidewall of the reservoir.

In the preferred embodiment, the elongate hollow member includes a plurality of diametrically opposed longitudinal slots disposed in spaced relation to each other along the length of the elongate member that is adapted to reside within a reservoir attached to the receptacle. These elongate slots facilitate the flow of aerosolized powder to and through the barrel portion of the device, assist in the avoidance of clogging of the elongate hollow member and insure that as much of the powdered material stored in the reservoir as possible is sprayed prior to the necessity of refilling the reservoir or substituting a new reservoir. In this regard, it has been found that several large cross-sectional area holes in the elongate hollow member work as well or better than a greater number of small holes disposed along the elongate hollow member. Accordingly, it is to be understood that the specification of slot shaped holes in this specification is for convenience of manufacture only, and that other cross-sectional hole configurations will work equally as well.

Finally, the present invention contemplates that appropriate gaskets and seals will be provided between the various parts to prevent leakage of propellant gas, powder or aerosolized powder from the device in ways that are generally well understood in the art.

Therefore, it will be apparent to those skilled in the art that when the internal volume of a reservoir attached to the housing contains a quantity of powdered material, a quick and forceful collapse of the hollow cavity of the handle by the fingers of a user causes the content of the hollow cavity (usually air) to be forced through the outlet from the handle into the receptacle through the conduit in the connecting portion of the housing. The entry of this pulse into the internal volume of the reservoir through the inlet opening at the bottom of the receptacle around the large-headed one-way valve port agitates the stored powder contained in the reservoir causing at least a portion thereof to become aerosolized (i.e., entrained within the pulse passing through the stored powder). Further, since the entry of the pulse into the reservoir so as to pass through the stored powder increases the internal pressure in the reservoir, at least part of the gas then contained in the reservoir with powder entrained therein is forced into the elongate hollow member via its inner open end as well as via such of the slots therein as are not clogged by the stored powder. Further, an additional quantity of the powder from within the stored powder mass is forced into the elongate hollow member through at least some of the slots therein that are covered by the stored powder mass as a result of the agitation of the powder mass caused by the pulse passing through it.

The result of the foregoing is that a portion of the powder contained in the reservoir is aerosolized, and a portion of the aerosolized and a portion of the non-aerosolized powder are both forced out of the reservoir into and through the barrel portion in the form of an aerosolized powder stream for ultimate discharge from the open end of the barrel portion of the housing (or the open outer end of a cannula extending outwardly from the barrel portion of the housing).

Thereafter, when the user releases the collapsing force on the handle, the resilient nature of the material from which the handle walls is made returns the handle to its original non-collapsed shape while drawing outside air or some other propellant into the hollow handle via its selectively operable inlet (typically a one-way inlet valve).

BRIEF DESCRIPTION OF THE DRAWINGS

These and other features and advantages of the present invention will become more apparent to those skilled in the art in view of the following detailed description of a preferred embodiment thereof rendered in conjunction with the appended drawings wherein:

FIG. 4 is a perspective view of a preferred embodiment of a powdered material spraying device in accordance with the present invention;

FIG. 5 is a side elevational view in partial cross-section of the preferred embodiment of the present invention shown in FIG. 4;

FIG. 6 is a side elevational view in partial cross-section of an alternative embodiment of the present invention including a cannula disposed in the barrel portion of the housing;

DETAILED DESCRIPTION OF PREFERRED EMBODIMENT

Figure 1:
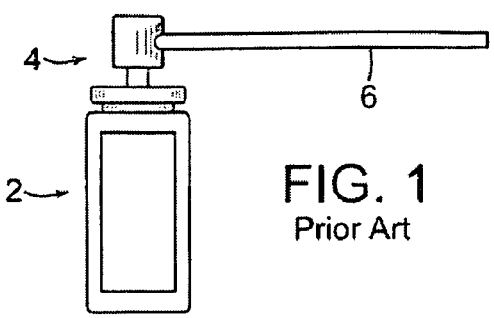
FIG. 1 is a schematic side elevational view of a prior art powder sprayer including a reservoir containing powder and a quantity of gas under pressure, a release button and a directional conduit.

Turning now to the drawings and particularly to FIGS. 4 to 8, there is shown a powder spray device generally indicated at 100 in accordance with a preferred embodiment of the present invention. The powder spray device 100 is of the so-called "puffer" type, and includes a housing 102 having various internal conduits, connections and the like that will be described in further detail below, a collapsible bulb 104 formed of a resilient material such as rubber, and a powdered material storage reservoir 106. The basic operational steps required for the use of this device include (i) generating a gas pulse, (ii) injecting the gas pulse into the quantity of powdered material contained in the powdered material storage reservoir 106 attached to a receptacle portion 108 formed in the housing 102 so as to aerosolize at least part of the stored powdered material, and (iii) discharging at least part of the so aerosolized powdered material from the reservoir 106 through an output of the housing 102 for spraying onto a target surface (not shown). As has been discussed generally hereinabove, however, the present invention provides a device for accomplishing these operations in a greatly improved, efficient and convenient manner not heretofore available in the art.

In the preferred embodiments of the invention illustratively shown in FIGS. 4 to 8, the reservoir 106 (best see in FIG. 8) is an elongate hollow container 110 having a closed, generally hemispherical end 112 and an open inner end 114. Further, the outer surface 115 of the reservoir 106 adjacent to its open end 114 is provided with engagement means generally indicated at 116 for interaction with a storage cap 117 or with the receptacle portion 108 of the housing 102. These interactions respectively securely, sealingly, yet easily removably, (i) seal the open end of the reservoir during periods of powdered material storage therein, and (ii) maintain the reservoir 106 in securely attached relation to the receptacle portion 108 of the housing 102 in the desired configuration.

In a particularly preferred form of the invention, the engagement means 116 for securing the reservoir 106 to the receptacle portion 108 of the housing 102 includes a pair of J-shaped or L-shaped slots generally indicated at 118 and 120 disposed diagonally opposite to one another in the outer surface 115 of the reservoir 106. More particularly, the longer leg 122 of each of the slots 118 and 120 (that extend radially into, but not through, the side walls of the reservoir 106) open into the open inner end 114 of the reservoir 106 on the opposite side of its sidewall from the powdered material receiving cavity 124. The longer legs 122 of the slots 118 and 120 extend along the outer surface 115 of the reservoir 106 substantially parallel to its longitudinal axis 126. The shorter legs 128 of the slots 118 and 120, on the other hand, extend generally circumferentially along the surface 115 of the reservoir 106 in a plane substantially normal to the longitudinal axis 126 of the reservoir 106. Thus, as will become further apparent below, the slots 118 and 120 in the outer surface 115 of the reservoir 106 may be engaged by corresponding projections 242 associated with the receptacle portion 108 of the housing 102 so as to maintain the releasable attachment and orientation of the reservoir 106 relative to the receptacle portion 108.

Alternatively, the J-shaped or L-shaped slots 118 and 120 may engage diametrically opposed, inwardly extending projections 128*a* from cylindrical sidewall 130 of a storage cap 117 having an open end 132 and a closed end 134. Accordingly, it will be seen that the reservoir 106 may securely contain a preselected quantity of powdered material (generally indicated at 136) separately from the housing 102 for example during sterilization and/or storage prior to its attachment to the receptacle portion 108 of the housing 102. Thus, it is to be understood that the present invention contemplates that the device may include one or a plurality of interchangeable reservoirs 106, and that each reservoir may be pre-filled, sealed, pre-sterilized and stored for removeable attachment to the receptacle portion 108 of the housing 102 as necessary and/or desired.

The housing 102, on the other hand, is a substantially pistol-shaped structure that includes a barrel portion generally indicated at 138, a handle portion generally indicated at 140 and a connecting portion generally indicated at 142 located between and connecting the barrel and the handle portions 138 and 140, respectively.

The handle portion 140 generically defines a hollow cavity, an inlet at its outer end selectively connecting the hollow cavity to the surrounding atmosphere and an outlet at its other end connecting the hollow cavity to the connecting portion. Further, the walls of the hollow cavity are constructed so as to be readily and easily grasped by a hand of a user, and also such that the hollow cavity can be easily and selectively collapsed by a user's hand so as to force the contents of the hollow cavity through its outlet. Also, the hollow cavity is constructed such that after it has been collapsed, it tends to resume its non-collapsed shape upon the release of the collapsing force of the user's hand. Further, this tendency of the collapsed handle portion to resume its non-collapsed shape results in a recharge of propellant into the hollow cavity through its inlet (i.e., air from the surrounding atmosphere enters the collapsed handle via a one-way inlet valve at its outer end as the resilience of the handle material causes the walls thereof to recover from their collapsed shape toward their normal shape).

In the particular preferred embodiment shown in FIGS. 4, 5 and 6, the handle portion 140 includes a rear wall 144, upper and lower front wall portions 146 and 148, side wall portions (generally shown at 149 in FIG. 4) connecting rear wall 144 and front wall portions 146 and 148 adjacent to the top and bottom of the handle portion 140, respectively, as well as a bottom wall portion 150 defining an opening 152 therein. Thus, in the particularly preferred embodiment shown in the drawings, these walls of the handle portion together define a support structure for a hollow bulb 154 made of a resilient material such as rubber. This support structure is described in greater detail below.

The bulb 154, on the other hand, includes a central hollow portion 156 having thin walls 158 and a basically elliptical longitudinal cross-section.

Further, the bulb 154 includes short projection 160 defining a central opening 162 into the interior (central hollow portion) 156 of the bulb 154 located at the top narrow end 164 thereof. In addition, a projection 166 substantially longer than the short projection 160 is located at the other narrow end 168 of the bulb 154. The projection 166 defines an opening 170 into the interior 156 of the bulb 154, and a one-way valve or the like, generally indicated at 172, is provided in association with the opening 170. One-way valve 172 is designed to allow the passage of air or some other propellant from outside the bulb into the bulb's interior (central hollow portion) 156, but to prevent the content of the bulb 154 from leaving the interior 156 thereof through the opening 170.

For example, one-way valve 172 may be formed as simple flap valve. In such a case, those skilled in the art will understand that a flap member (not specifically shown) would be attached to part of the periphery of the inner end 174 of the opening 170 so as to normally rest over a reduced diameter portion 176 of the opening 170. Given that construction of the one-way valve 172, it will be understood by those skilled in the art that forces tending to collapse the hollow interior 156 of the bulb 154 would be prevented by the flap member from forcing the contents of the bulb outwardly through the opening 170.

However, once the interior of the bulb 156 is disposed in its collapsed state and the forces thereon tending to maintain its collapsed state are released, the resilience of the bulb structure tends to return the bulb to its non-collapsed configuration. This creates a partial vacuum within the interior 156 of the bulb 154, and that partial vacuum tends to draw air or some other externally available propellant into the interior 156 of the bulb 154 through the one-way valve 172. In other words, since the flap member of the valve is free to swing inwardly about its attachment to the wall of the opening 170, air or another propellant from the outside in this case is allowed to enter the bulb through the one-way valve in response the inward movement of the flap of the one-way valve induced by the partial vacuum created as the walls of the bulb tended to expand outwardly from their collapsed to their normal configuration. Of course, other types of one-way valves also could be positioned within the opening 170 without departing from the present invention in its broadest aspects.

Further, as also will be seen from FIGS. 4, 5 and 6, the bulb 154 and the walls of the handle portion 140 of the housing are sized relative to one another such that a central, rear portion of the bulb wall 158 rests generally against the fixed, rigid rear wall 144 of the handle portion (as shown in the drawings) and support ribs generally indicated at 177 may extend outwardly from the inner surface of fixed rear wall 144 so as to more securely orient and fix the disposition of the bulb relative to the walls of the handle portion. Also, the long, small diameter projection portion 166 of the bulb 154 is held in the pocket formed at the lower end of the rear wall 144 of the handle 140 by the lower portion of rear wall 144, the lower front wall 148, the connecting side wall portions (not specifically shown) and the bottom wall 150 with the opening 170 in the projection portion 166 of the bulb substantially aligned with the opening 152 through the bottom wall 150 to facilitate the inflow of air or other propellant into the bulb as discussed above.

The short, small diameter portion 160 at the other narrow end of the bulb 154, on the other hand, is disposed inwardly of the front wall 146 and the adjacent side wall portions (not shown) and also against interior supporting ribs generally indicated at 179 of the connecting portion 142. Hence, the projections 160 and 166 at the opposite ends of the bulb 154 are securely held by the framework provided by the various wall portions of the handle portion 140 of the housing 102 such that the central, narrow walled portion 156 of the bulb 154 is supported only along its rear side wall portion, i.e., as perhaps best seen in FIGS. 4, 5 and 6, the bulb forms the front and side surfaces of the handle portion 140 in such a manner that a user grasping the handle can easily collapse the bulb by exerting a force against the portion of the bulb defining the front surface of the handle toward the fixed rear wall of the handle portion of the housing.

The barrel portion, generally indicated at 138, of the housing 102 in the preferred embodiment of the invention depicted in the drawings is an elongate hollow shaft 180 centered on a longitudinal axis 181. The shaft 180 is open to the atmosphere at a free end 182 thereof and opens into the connecting portion 142 at its other end 184. Further, the interior cross-section of the shaft 180 is sized to receive an end portion 186 of a cannula 188 in snug friction fit therein. (See, FIG. 6)

Figure 7:
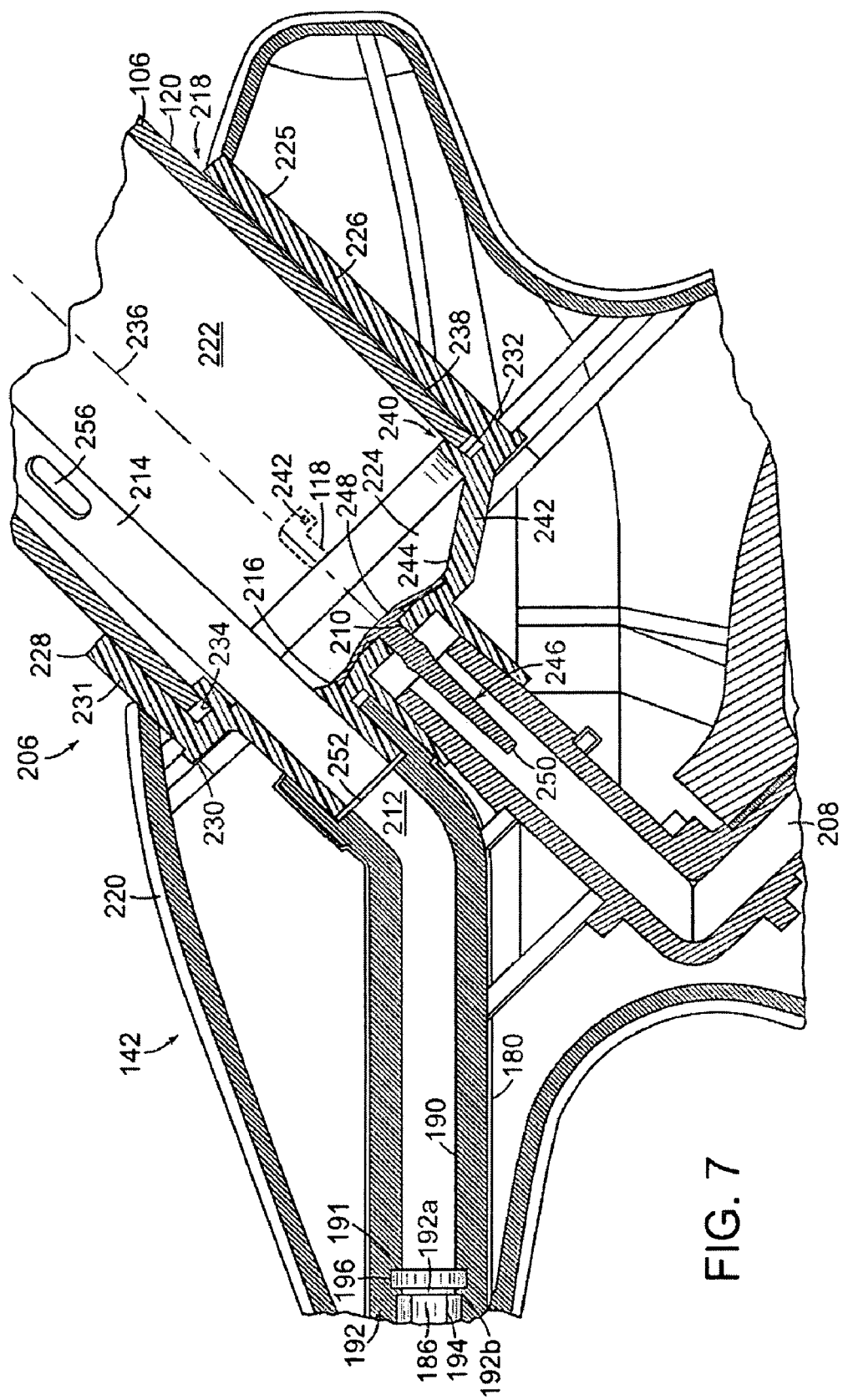
FIG. 7 is a side elevational view in enlarged cross-section of the connecting portion of a housing in accordance with the present invention showing the detail of the engagement of a receptacle therewith.
Figure 8:
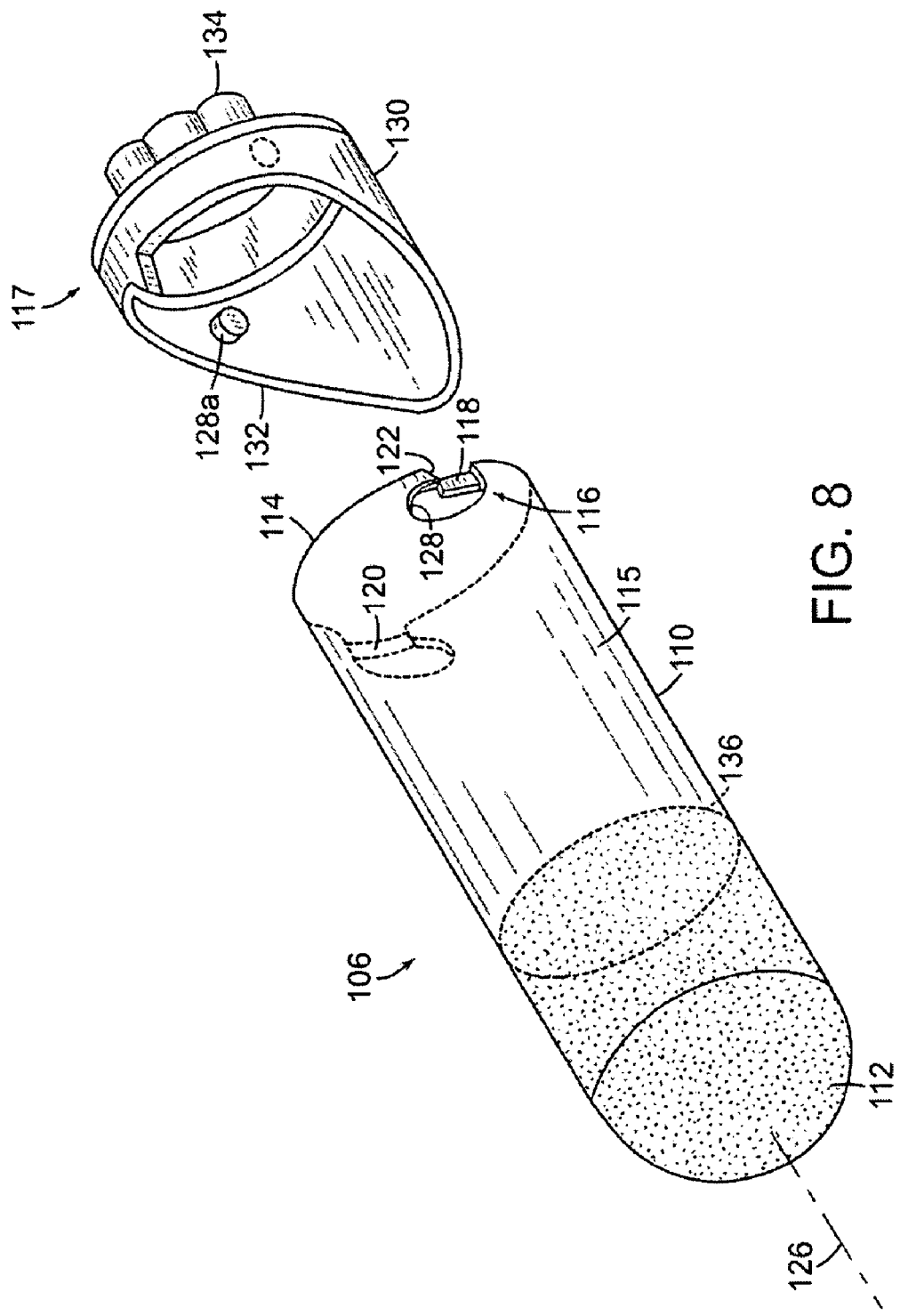
FIG. 8 is a perspective exploded view of a reservoir member and associated storage cap in accordance with the present invention.

Thus, in one version of the preferred embodiment of the present invention best shown in FIGS. 6 and 7, an end portion 186 of cannula 188 extends into the open end 182 of the barrel portion 138 of the housing 102. In this embodiment, the barrel portion 138 defines a reduced diameter portion 190 adjacent to the connecting portion 142 of the housing 102 so as to form an internal annular stop 191 against which the end of the cannula inserted into open end of the barrel abuts in the fully assembled condition. In the latter configuration, engagement means 192 may be provided on the outer surface 194 of the cannula adjacent to its inserted end 186 and on the inner portion 196 of the barrel shaft adjacent to the stop 191 that interact with one another to insure the secure disposition of the cannula in the shaft defined by the barrel portion. For example, as representatively shown in FIG. 7, these interacting engagement means may take the form of an encircling groove 192a adjacent the inserted end of the cannula, and one or more radially inwardly extending projections 192b from the interior of the shaft of the barrel portion that are designed to engage the groove in the cannula upon its full insertion into the barrel portion of the housing. Otherwise, the barrel portion of the housing constitutes an elongate shaft attached to, and communicating with, the connecting portion of the housing for directing the output aerosolized powdered material spray from the device.

The use of the cannula in the context of the present invention has been found to be particularly useful because it allows the output of the device to be placed directly into small, relatively inaccessible areas such as laparoscopic surgical sites. In those cases, the available area for movement of the device relative to the surface to be coated by the powder typically is quite small. Further, there also may be a need to orient the device in space such that the longitudinal axis of the barrel does not remain straight in use (i.e. there may be a need in some situations to bend the discharge opening (i.e., open end) of the cannula relative to its primary longitudinal axis, (for example, by pulling on an embedded guide wire in the wall of the cannula in a manner well known in the art and not particularly shown in the drawings). In the latter case, direct visualization of the surface(s) to be coated with the powder by the user may be either difficult or impossible.

To partially compensate for these difficulties, in addition to the features discussed above, the present invention also contemplates that the outer end portion 198 of the cannula may be provided with a diffuser 200 either built into the cannula or attached thereto at its outer open end so as to optimize the spray pattern of the emitted aerosolized powder. Of course, a similar diffuser structure also may be provided at the outlet from the barrel portion regardless of whether or not a cannula is used so that the output spray pattern may be optimized in all cases.

In a particularly preferred form, the geometry of the diffuser 200 is such that the interior diameter of a cross-section of the cannula, or a fitting attached to the outer open end thereof, smoothly narrows to a predetermined extent and thereafter expands back to its original diameter over a predetermined length. Thus, in one specifically preferred embodiment, the outer end portion of a 0.18 inch diameter cannula narrows to a diameter of about 0.15 inches over a cannula length of about 0.35 inches. It will be understood by those skilled in the art, however, that the optimal design for diffusion of the aerosolized powder being discharged from the device may vary according to the particular size of the cannula used and the type and size of the powder particles entrained in the aerosolized powder flow among other variables.

Turning now to the connecting portion 142, it will be seen from FIG. 4 that the lower rear part 201 of the connecting portion 142 of the housing 102 defines a grip portion 202 adjacent to the handle portion 140 that is contemplated to include an outer contour designed to receive the portion of the operator's hand joining the operator's thumb and forefinger while the lower side portions 204 thereof are contoured to receive the operator's thumb and forefinger, respectively. Hence, the housing is easily grasped and held by the operator in a manner analogous to the conventional gripping of the handle of a pistol.

Otherwise, as best seen in FIG. 7, the connecting portion 142 includes a receptacle 206, a conduit 208 connecting the output 162 of the handle portion 140 to an input 210 of the receptacle 206, an internal output shaft 212 connected to the shaft 180 of the barrel portion 138, and a hollow, elongate output member 214 extending from the internal output shaft 212 within the connecting portion through an output opening 216 in the receptacle 206 and projecting outwardly from the receptacle a distance substantially equal to the longitudinal length of the reservoir between the open and hemispherical ends thereof.

The receptacle 206 basically constitutes a cavity 218 extending into the outer surface 220 of the connecting portion 142 that includes two parts 222, 224. The first of these parts 222 constitutes an outer cavity portion having a substantially circular cross-section extending into the surface of the connecting portion.

More specifically, in the preferred embodiment shown in the drawings, the portions 225 of the sidewall 226 of the circular cavity 222 located closest to the rear of the housing have a greater axial length than the opposing portions 228 thereof due to the surface contour chosen in this embodiment for the connecting portion 142. Accordingly, when a reservoir 106 is disposed in the receptacle 206, a larger portion of the axial length of the reservoir is supported from below and behind it than it is supported from above and forward of it. In addition, the base 230 of the first part 222 of the receptacle 206 is disposed in a plane substantially normal its sidewalls 231. In particular, at the base 230 of the first cavity part 222 of the receptacle 206 spaced radially inwardly a distance slightly less than the thickness of the sidewall of the reservoir at its open end is a short inner wall 232 having an inner surface 234 that slants inwardly toward the longitudinal axis 236 of the circular cavity from its bottom edge to its top edge. This inner surface 234 of short inner wall 232 acts to define with the inner surface 238 of the outer sidewall 231 of the first cavity part 222 of the receptacle 206 and its base 230 a circular channel 240 adjacent to the base of the first portion of the receptacle that is adapted to receive the sidewall edges located at the open end of the reservoir.

Furthermore, inwardly extending diagonally opposed projections 242 are located on the outer sidewall 238 of the first cavity part 222 of the receptacle 206. The interaction of the first cavity part 222 of the receptacle 206 and a reservoir element 106 is such that as the open end of the reservoir 106 is inserted into the first cavity part 222 of the receptacle 206, the inwardly extending projections 242 engage the slots 118 in the outer surface 115 of the reservoir 106 and the inner diameter of the open end 114 of the reservoir 106 is brought into engagement with the inner slanted surface 234 of the short wall 232 of the channel 240 at the base of the first cavity part 222 of the receptacle 206.

Then, as a result of further pushing the reservoir 106 axially into the receptacle 206 until it can be twisted about its longitudinal axis such that the projections 242 from the sidewall enter the shorter length legs of the J-shaped or L-shaped slots 118 in the exterior of the reservoir 106, the inner diameter of the reservoir 106 at its open end 114 is forced against, and deformed slightly outwardly so as to be releasably locked, against the inner slanted wall surface 234 of short wall 232 of the channel 240. Hence, the open end of the reservoir is disposed in the channel in secure and sealed engagement with the receptacle.

The remainder (i.e., the second cavity part 224) of the receptacle 206 includes a cavity having a generally flat bottom portion 242 connected to the base 230 of the first cavity part 222 at the inner side of the short wall 232 by an outwardly curved sidewall 244. This second cavity part 224 of the receptacle 206 extends into the connecting portion symmetrically about the longitudinal axis 236 of the first cavity part 222 below the level of the base 230 of the channel 240. The opening 210 in the flat bottom portion of this cavity part 224 constitutes the inlet to the receptacle that is connected to the handle portion 140 of the device by an appropriate conduit 208 within the connecting portion 142.

In addition, a one-way valve 246, in the preferred embodiment a so-called "mushroom" valve, is disposed in the conduit connecting the handle portion to the inlet of the receptacle to the handle. This valve has a large head 248 that overlaps the entire circumference of the inlet opening in the bottom of the receptacle and a stem portion 250 residing in, and interacting with, the conduit such that the stem/head combination is allowed to move outwardly into the receptacle a small distance in response to output propellant pulses from the handle such that the input gas flows into the receptacle around the base of the large head 248. Otherwise, when no input pulse is flowing through the conduit, the enlarged head of the valve closes down over the inlet opening in the bottom of the receptacle to prevent a backflow of powdered material from the reservoir into the connecting conduit or into the handle portion.

Above the flat-bottomed portion of the inner cavity of the receptacle, the hollow elongate output member 214 extends through, and is secured in, the curved sidewall portion 244 of the second cavity part 224 of the receptacle substantially parallel to the longitudinal axis of the circular first cavity part 222 of the receptacle. As noted above, one open end 252 of this elongate hollow member communicates with the internal end of the internal channel 212 defined by the connecting portion that opens at its other end into the hollow barrel portion 180. The other open end 254 of the elongate, hollow output member 214 resides at a distance outwardly from the receptacle such that when a reservoir is mounted in the receptacle that other open end resides substantially adjacent to the closed hemispherical end of the reservoir and the elongate member is disposed substantially along the sidewall of the reservoir.

In the preferred embodiment, the elongate hollow member 214 includes a plurality of diametrically opposed longitudinal open slots 256 disposed in spaced relation to each other along the length of the elongate member that resides within a reservoir attached to the receptacle. These elongate slots facilitate the flow of aerosolized powder to and through the barrel portion of the device, assist in the avoidance of clogging of the elongate hollow member and also insure that as much of the powdered material stored in the reservoir as possible is sprayed prior to the necessity of refilling the reservoir or substituting a new reservoir. In this regard, Applicants have discovered that several large cross-sectional area holes in the elongate hollow member work as well or better for these purposes than a greater number of small holes disposed along the elongate hollow member. Accordingly, it is to be understood that the specification of slot shaped holes in this specification is for convenience of manufacture only, and that other cross-sectional hole configurations will work equally as well.

It also is to be understood that the conduits connecting the handle portion to the inlet of the receptacle typically are disposed within defined channels in the connecting portion. These defined channels may be entirely enclosed, or if desired, may be formed by aligned openings in a plurality of interior support ribs provided to support and maintain the shape of the outer wall of the connecting portion in the embodiment shown in the drawings. Similarly, it will be understood by those skilled in the art that the housing and reservoir of this invention conveniently may be formed of injection molded plastic or the like in the form of two longitudinal halves. In that case, the halves of the housing after the disposition of the conduits in the connecting portion and the bulb in the handle portion typically are connected by adhesives and/or frictional mechanical engagement all along the mating edges thereof, or if desired, the joinder of the halves of the housing may be accomplished at distinct locations along the edges thereof in any convenient conventional manner such as projecting pins adjacent one mating edge engaging corresponding sockets adjacent the other mating edge or by heat welding.

Having now described a preferred embodiment of the powdered material delivery device of the present invention, it will be understood that the powdered material delivery device of the preferred embodiment just described operates substantially as follows:

First, a desired quantity of powder is placed in the reservoir and the reservoir is either capped for storage and later use, or assembled with the housing. In either case, the slots in the outer surface of the reservoir adjacent to its open end are engaged by inwardly extending projections from surrounding circular walls such that the projections engaging the slots and slide along the longer legs thereof until the reservoir can be twisted on its longitudinal axis so as to lock the projections in the transverse portions of the slots. In the case of the cap, a gasket or the like (not specifically shown) placed against the closed end of the cap may serve as a seal that is compressed by the open end of the reservoir during the engagement of the cap therewith. In this way, moisture and other contaminants may be sealed out of the stored powdered material. Indeed, the reservoir containing powdered material can be pre-sterilized and retained in a sealed container until ready for use if desired.

The mounting of the reservoir onto the housing is similar. Specifically, the open topped reservoir containing a preselected quantity of powdered material is held substantially vertically. Then, the housing is inverted so as to insert the portion of the elongate member extending from the receptacle into the reservoir first. Thereafter, the reservoir is inserted into the outer cavity of the receptacle until is open end engages the channel at the base of the outer portion thereof. At that point, the open end of the reservoir is forced into the channel of the receptacle so as to create a sealed engagement therewith. This can be accomplished using a compression gasket (not shown) within the channel, but as discussed above, in the preferred embodiment this sealed engagement is achieved by forcing the open end of the reservoir against a slanted wall of the channel so as to cause it to deform slightly outwardly. This deformation of the open outer end of the reservoir causes it to tightly engage the inner wall of the channel thereby forming a seal. In this regard, it will be understood by those skilled in the art that by selecting the length of the longer legs of the slots in the exterior of the reservoir relative to the depth of the outer portion of the receptacle appropriately, the engagement of the projections from the sidewall of the outer portion of the receptacle with the transverse portions of the slots can be made to secure and maintain the compression fit of the open end of the reservoir over the lager diameter portion of the inner wall of the receiving channel in the reservoir as well as insuring the secure attachment of the reservoir in the receptacle portion of the housing.

Thereafter, the housing is rotated to its normal position with the reservoir extending at an acute (substantially 45°) upward angle from the connecting portion of the housing relative to the longitudinal axis of the barrel portion thereof. It also will be understood that as this is occurring, the powdered material located in the reservoir shifts from being piled on the bottom of the reservoir to a disposition piled on the receptacle with the top surface of the powder assumes a disposition slanted at an acute angle to the longitudinal axis of the reservoir.

Hence, the relative disposition of the open end of the elongate member originally inserted into the reservoir's open end and thence into the stored agglomerated powdered material therein also changes such that that open end becomes disposed in an open headspace area adjacent to the hemispherical bottom of the reservoir.

Further, according to the intended usage of the device, a cannula may be inserted into the barrel portion so as to engage the annular stop at the inner end of the barrel portion, if desired. Also, the groove in the outer surface of the cannula adjacent to the open end thereof inserted into the barrel portion may be engaged by radial projections from the inner barrel portion wall to secure the cannula in place.

As briefly mentioned above, when the device is assembled as just described, the internal volume of powdered material in the reservoir has a generally horizontally disposed surface within the reservoir that is located below the open end and at least some of the longitudinal slots in the elongate hollow member. Thus, a quick and forceful collapse of the hollow cavity of the handle by the fingers of a user will cause the content of the hollow cavity (usually air) to be forced through the outlet of the bulb, through the conduit, past the one-way "mushroom" valve and into the powdered material contained in the reservoir and the cavity formed by the receptacle in the surface of the connecting portion of the housing. In this regard, it will be understood that the sealed nature of the connection of the bulb to the conduit is contemplated to resist leakage of the bulb content as it is forced out of the bulb and through the conduit. Similarly, the one-way "mushroom" valve disposed in the conduit adjacent to and covering the side edges of the inlet located in the innermost base of the receptacle resists leakage of the stored powder into the conduit connection to the handle portion of the housing mechanically in its closed position and by virtue of the outward flow of propellant therethrough in its open position.

More particularly, the content of a pulse generated by the collapse of the handle enters into the internal volume of the reservoir through the inlet around the enlarged head of the one-way "mushroom" valve at an accelerated velocity all around its circumference. Consequently, the propellant pulse entering the bottom of the receptacle agitates the agglomerated stored powder then contained in the receptacle and the reservoir thereby causing at least a portion of that powdered material to become aerosolized (i.e., entrained within the pulse passing through the stored powder).

Further, since the entry of the pulse into the reservoir so as to pass through the stored powder increases the internal pressure in the reservoir, part of that content of the pulse (typically air) with powder entrained therein is forced into the elongate hollow member via both its inner open end and such of the slots therein as are not covered by the stored powder for output as an aerosolized powder spray. Still further, additional powder from within the stored powder mass also is forced into the outlet extension through such of the slots therein as may be covered by the stored powder mass.

Incidentally, this increase in pressure combined with the presence of the slots in the sidewall of the elongate, hollow member also acts to dislodge any clogging within the elongate, hollow member that may occur, particularly the clogging of the open end of the elongate hollow member that often occurs during the initial insertion of the elongate member into the agglomerated powdered material mass stored in the reservoir prior to the attachment of the reservoir to the receptacle and the subsequent repositioning of the housing in its normal spatial orientation (i.e., with its handle portion extending downwardly from the connecting portion).

Figure 2:
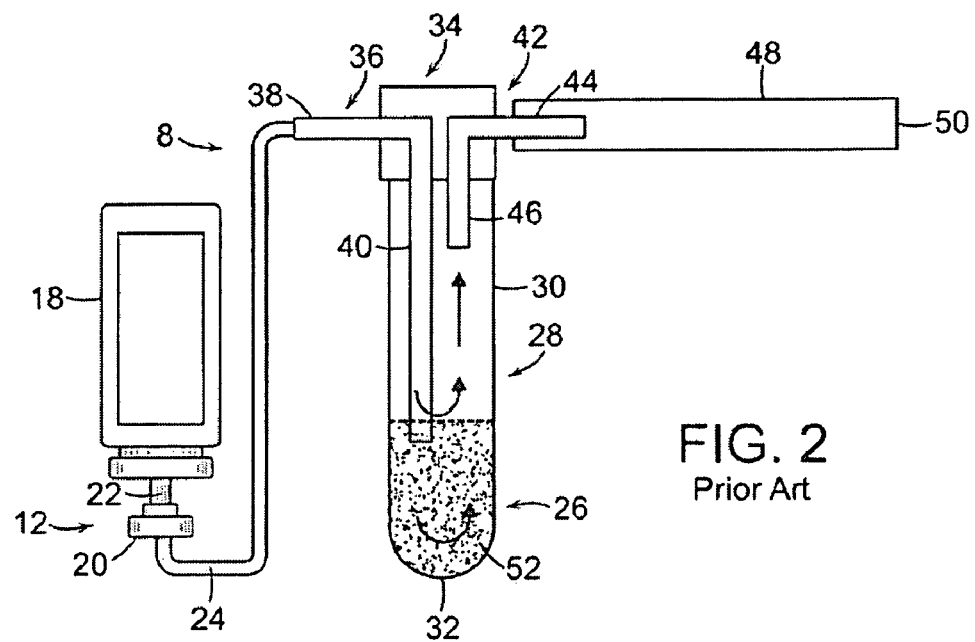
FIG. 2 is illustrative schematic side elevational view in partial cross-section of a prior art powder spray device utilizing a source of metered pressurized gas and a so-called "Wolf" powdered material sprayer.
Figure 3:
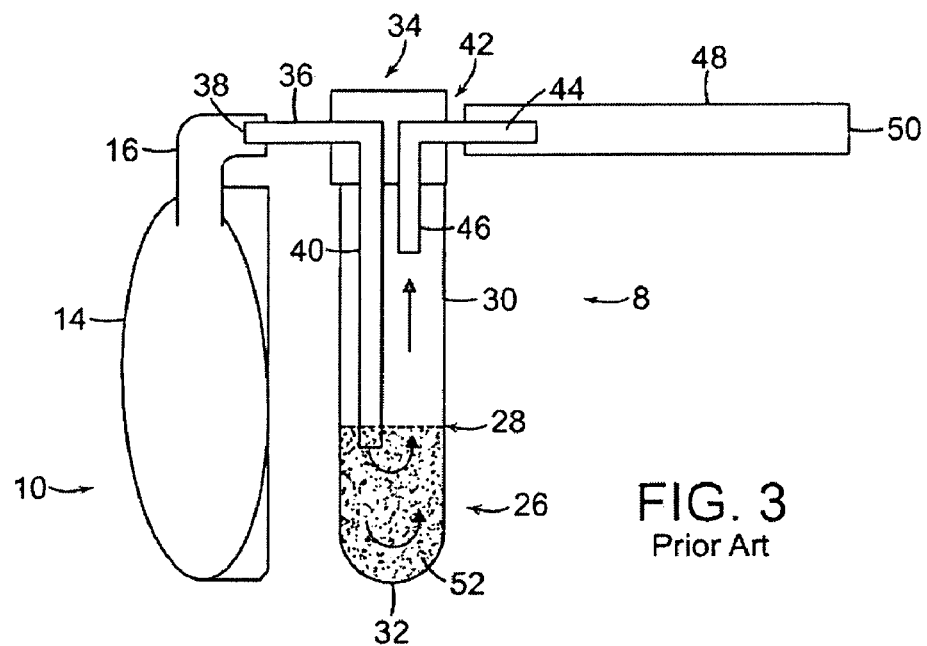
FIG. 3 is a schematic side elevational view in partial cross-section of a prior art powder spray device utilizing a hand operated pump and a so-called "Wolf" powdered material sprayer.

In this way, even though the agitation of the powder within the reservoir does not include the same circular airflow within the powder mass adjacent to the hemispherical closed end of the reservoir as was present in the prior art (see FIGS. 2 and 3), adequate powder spray flow rates and other advantages of the present invention nevertheless still can be achieved. Indeed, it has been found that while quick, fast and forceful collapsing forces applied to the handle achieve the greatest powdered material spray amounts per pulse (i.e., the so-called maximum dosage rate of the device), the device of the present invention also can accommodate smaller pulses successfully as long as the induced pressure levels thereof exceed a predetermined minimum. This is important because as also briefly mentioned above there is a tendency by those performing "close" and delicate tasks to minimize at least the extent, if not the force, of their movements. Thus, for example, a surgeon spraying an anti-adhesion powder into a surgical wound might be expected to exert multiple small collapsing movements of his fingers against the outer surface of the bulb rather than the larger quick and forceful motions that would be adequate to completely collapse the bulb in an effort to better direct the flow of powdered material spray to different target surfaces within a wound in a controlled manner with the least possible inflicted trauma to the tissue.

Thereafter, when the user releases the applied collapsing force on the handle, the resilient nature the material forming the bulb tends to return the bulb to its original non-collapsed shape while drawing outside air or some other propellant into its hollow interior via its selectively operable inlet (typically a one-way valve).

In addition, it has been found that the above-described construction and advantages of the present invention may be optimized when the relative dimensions of the various parts of the device are designed to complement one another (i.e., for example, when the volume of the interior of the bulb is matched to the size of the reservoir and the diameters of the various propellant and powder spray conveying conduits).

Further, it has been found that for present commercial marketing reasons related to the typical parameters encountered in medicinal powdered material spray contexts, the volume of the reservoir should be such that at least about 2 grams of powder can be stored in the reservoir and that on the order of about 95% of that amount can be output as an aerosolized spray without clogging even in a pressurized environment. This quantity of powdered material is believed to meet or exceed the requirements presently encountered in most surgical procedures such as, for example, the coating of an operative site with an anti-adhesion powder prior to closing the surgical wound. Of course, however, those skilled in the art will readily recognize that these parameters may be varied as the particular usage context dictates without departure from the present invention in its broadest aspects.

Further still, it has been found that the device of this invention should be capable of spraying powders composed of particles within a particle size range of at least about 100-425 μm so as to be capable of handling a wide range of mixtures of powdered components. In this respect as well, the size and number of slots in the inwardly extending portion of the elongate hollow member have been found to work the best when 2 rows of 2 slots disposed opposite to each other are provided, each slot being on the order of about 0.062"×0.15" in a 0.18 inch diameter elongate hollow member. Those skilled in the art will understand that the openings in the sidewall of the elongate hollow member are preferably formed as slots for ease of manufacture, and that other geometric shapes of the openings in the sidewall of the elongate hollow member will work in a similar manner. Further, such comparatively large area openings in the sidewall of the elongate hollow member work at least as well, if not better, than a large number of smaller area openings disposed along the length of the elongate hollow member within the reservoir. This presently is believed to arise from the fact that the provision of larger area openings in the sidewall of the elongate hollow member are less restrictive of the flow of aerosolized and non-aerosolized powdered material therethrough than are smaller cross-sectional area openings.

Still other parameters also are deemed to be important. Among these parameters are the dose rate (i.e., the quantity of powder delivered in response to each "complete" collapse of the handle—presently preferred to be about 0.03 g to about 0.2 grams for each collapse of the handle); the spray pattern (i.e., the size of a delivered spot of powder at a predetermined distance from the outlet of the cannula or diffuser—presently preferred to be about 0.7 inches to about 0.81 inches at 2 inches from the outlet of the device); the coverage rate (i.e., the amount of powder that can be delivered by the device per unit area at a predetermined distance from the outlet of the cannula or diffuser for no more than two successive "complete" collapses of the handle—presently preferred to be about 2.7 mg/cm$^2$ to about 3.1 mg/cm$^2$); and the spatial orientations achievable with the device without adverse impact upon its other operational parameters—presently a tilt of the longitudinal axis of the barrel portion of between about 0° and 90° below the horizontal, and most preferably between at least about 20° below the horizontal to about 70° below the horizontal, so as to facilitate the manipulation of the outlet of the device relative to the area to be coated by the powder and the delivery of the powder at such non-horizontal spatial orientations. Indeed, as alluded to briefly above, these angles are the angles at which a surgeon would typically desire to point the barrel of the pistol shaped housing toward a wound in a patient located on an operating table or the like, as well as providing enough freedom for the surgeon to manipulate the device so as to best direct the output spray to the desired target area. Similar considerations also apply to the utilization of the device for spraying powdered materials into so-called "closed" laparoscopic wounds that are not readily visible to the surgeon except through a fluoroscope or the like.

Therefore, the intent of the present invention is to provide a self-contained, single-hand-held, single-hand-operable powder delivery device suitable for both topical powder application and powder delivery onto target surfaces, particularly the surfaces of small, hard to reach areas including areas not visible to the powder delivery device operator. The foregoing specification describes one preferred embodiment of a device in accordance with the present invention that accomplishes those goals. However, in light of the foregoing specification those skilled in the art will readily recognize that numerous changes, modifications, variations, alterations and the like can be made to the preferred embodiment that is herein described without departure from the present invention in its broadest aspects. Therefore, it is to be understood that the foregoing specification is presented by way of illustration only, and not by way of limitation, and also that the scope of the present invention is to be understood as being defined only by the following claims.

What is claimed is:

1. A powder delivery device, comprising:
  a powdered material reservoir defining an internal volume adapted to receive and store a quantity of powdered material, said reservoir including an elongate body, said body having a reservoir longitudinal axis, a closed outer end and an open inner end; and a substantially pistol-shaped housing, said housing including a handle portion, a barrel portion and a connecting portion between said handle portion and said barrel portion;

said handle portion defining a hollow cavity, a first inlet selectively connecting said hollow cavity to the surrounding atmosphere and a first outlet connecting said hollow cavity to said connecting portion, wherein at least part of said handle portion is formed of a resilient material such that said hollow cavity may be selectively collapsed by an inwardly directed force applied by a user's hand grasping said handle portion so as to expel a content of said cavity through said first outlet, and wherein after collapse, said resilient material part is selectively restored to its non-collapsed configuration upon the release of said inwardly applied force by the resilience of said resilient material in combination with a content input into said cavity selectively received through said first inlet;

said barrel portion defining an open ended, elongate, hollow shaft centered on a barrel longitudinal axis, said shaft opening to the atmosphere at said open end thereof and opening into said connecting portion at the other end thereof; and said connecting portion defining a receptacle adapted to securely, sealingly and removably receive said open end of said reservoir and to hold said reservoir with its reservoir longitudinal axis disposed at a rearwardly extending upward angle relative to said barrel longitudinal axis of said barrel portion opposite to said handle portion; including internal conduit means joining said first outlet of said handle portion to a second inlet located in said receptacle; and including an elongate, hollow element extending through a second outlet located in said receptacle so as to open at one end into an end of a passageway in said connecting portion that opens at its other end into said shaft of said barrel portion, and also extending outwardly from said second outlet at substantially the same angle to said barrel longitudinal axis as said reservoir longitudinal axis when said reservoir is mounted in said receptacle to an open end, said outwardly extending portion of said elongate, hollow member further defining a plurality of opposed openings located at spaced intervals along its length;

whereby, when said internal volume of said reservoir contains a quantity of powdered material and said reservoir is mounted in said receptacle, a collapse of said hollow cavity causes a content of said hollow cavity to be forced into said internal volume of said reservoir in the form of a pulse so as to aerosolize a portion said powdered material stored in said reservoir and to cause at least some of said aerosolized powdered material to be discharged from said open end of said barrel portion via said open end and said openings in said elongate, hollow member, said internal passageway of said connecting portion and said shaft of said barrel portion.

2. The powder delivery device according to claim 1, wherein said reservoir defines J-shaped or L-shaped slots in opposing portions of an outer surface of its sidewall for engagement with projections provided in said receptacle, a longer leg of each of said J-shaped or L-shaped slots opening into said open end of said reservoir and extending along said sidewall substantially parallel to said reservoir longitudinal axis and a shorter leg of each of said slots extending from a closed end of each of said longer legs circumferentially in the same direction around part of said reservoir.

3. The powder delivery device according to claim 1, wherein said connecting portion defines a second substantially hollow cavity, and said conduits and said passageway are supported in said second substantially hollow cavity by internal rib members.

4. The powder delivery device according to claim 1, wherein first inlet comprises a one-way content intake valve.

5. The powder delivery device according to claim 1, wherein said second inlet comprises an opening into said receptacle containing a one-way propellant pulse inlet valve for when said reservoir is attached to said receptacle allowing propellant pulses to enter said open end of said reservoir, and for when propellant pulses are not flowing through said conduit preventing powdered material in said reservoir from entering said conduit or said cavity in said handle portion.

6. The powder delivery device of claim 1, wherein said receptacle defines an outer cavity having a sidewall including a lower edge, an annular base extending radially inwardly from said lower edge of said sidewall, and an inner wall portion extending axially outwardly from an inner edge of said annular base substantially parallel to, but a distance shorter than the smallest axial dimension of, said sidewall such that an axially outwardly facing open groove is located adjacent to said base in said connecting portion of said housing, said sidewall of said cavity defines a substantially circular cross-sectional area, and said outer cavity is adapted to receive said open end of said reservoir in said groove and to support said reservoir in said connecting portion of said housing such that said reservoir longitudinal axis is disposed at about 45° to said barrel longitudinal axis.

7. The powder delivery device of claim 6, wherein said inner wall portion of said outer cavity includes an inner surface that tapers radially outwardly from its axially outermost edge to its axially innermost edge such that when said open end of a reservoir engages said groove, said open end of said reservoir engages said tapered surface at a position located axially outwardly of said annular base such that when said reservoir thereafter is forced axially inwardly toward said base, said tapered surface tends to radially compress toward said reservoir longitudinal axis and said open end of said reservoir tends to radially flare outwardly relative to said reservoir longitudinal axis, whereby said reservoir may be sealingly attached to said receptacle.

8. The powder delivery device of claim 7, wherein said receptacle and said reservoir respectively include portions adapted to interact with one another in order to releaseably maintain said open end of said reservoir in sealed engagement with said groove.

9. The powder delivery device of claim 7, wherein said receptacle further comprises an inner cavity extending axially inwardly from an inner periphery of said base of said outer cavity, said inner cavity having a radially inwardly curved sidewall connecting said inner periphery of said base to a substantially flat bottom portion, wherein said second inlet enters said receptacle through said bottom portion of said inner cavity and said second outlet exits said inner cavity through said curved sidewall at a position located substantially vertically upwardly relative to said second inlet opposite said handle portion of said housing.

10. The powder delivery device according to claim 1, wherein said handle portion comprises a generally elliptical, hollow bulb formed of a resilient material mounted in a support structure;

said bulb comprising in aligned relation along a bulb longitudinal axis a first end portion and a second end portion connected by a hollow, thin-walled portion;

said first end portion having a first length, a first peripheral cross-section perpendicular to said first length and defining an open ended first passageway centered on said bulb longitudinal axis;

said second end portion having a second length longer than said first length, a second peripheral cross-section of similar maximum diameter to said first peripheral cross-section, and defining a second passageway centered along said bulb longitudinal axis containing a one-way valve so oriented as to allow passage through said second passageway only in an axial direction toward said first passageway in said first end portion; and said thin-walled portion defining a symmetrical cavity centered on said bulb longitudinal axis having a substantially truncated elliptical cross-section measured in a plane containing said bulb longitudinal axis, and said support structure comprises a rear wall connecting said connecting portion to a pocket at an outer end of said rear wall adapted to receive and hold said second end portion of said bulb with said second passageway in said second end portion aligned with an opening formed in a base of said pocket, and walls extending from a side of said connecting portion substantially opposite said receptacle adapted to receive an hold at least a front part of said first portion of said bulb such that said first passageway therein is in communication with said internal conduit means located in said connecting portion;

whereby said thin-walled portion of said bulb defines front, left and right sides of said handle portion such that said symmetrical cavity of said bulb can be collapsed by a user's hand grasping said handle portion of said device so as to force a content of said symmetrical cavity of said bulb into said reservoir through said internal conduit means.

11. The powder delivery device of claim 1, wherein said barrel portion defines an outer hollow shaft portion having a first diameter and an inner hollow shaft portion having a second diameter smaller than said first diameter, said inner and outer hollow shaft portions both being centered on the same barrel longitudinal axis and connected by a radially extending wall portion, wherein said outer shaft portion is adapted to receive and hold one end of an elongate cannula against said radially extending wall portion.

12. The powder delivery device according to claim 1 further comprising:

an open ended, elongate cannula associated with said barrel portion of said housing defining an open lumen extending therethrough, said cannula having a substantially constant internal diameter centered on a cannula longitudinal axis, including a first portion adjacent to an inlet one of said open ends substantially fixedly disposed within said elongate, hollow shaft of said barrel portion of said housing with said cannula longitudinal axis substantially aligned with said barrel longitudinal axis, and including a second portion adjacent an outlet one of said open ends projecting outwardly from said open end of said shaft of said barrel portion of said housing; and a diffuser associated with said outlet open end of said cannula, said diffuser defining an extension of said lumen of said cannula the diameter of which gradually narrows and thereafter gradually widens as it extends outwardly from said outlet open end of said cannula so as to achieve a desired spray pattern exiting from said powder delivery device as measured at a preferred spray initiation distance from a target surface.

13. The powder delivery device according to claim 11, wherein said cannula defines a circumferential groove adjacent the end thereof inserted into said barrel portion, and said outer hollow shaft portion of said barrel portion of said housing defines a plurality of radial inwardly extending projections disposed circumferentially along an interior wall of said outer shaft portion in axially outwardly spaced relation to said radial wall portion such that when said cannula is inserted into said outer shaft portion of said barrel portion of said housing, the end of said cannula adjacent to said circumferential groove abuts said radial wall portion of said barrel portion of said housing and said inwardly extending projections engage said circumferential groove so as to tend to lock said cannula in said outer shaft portion of said barrel portion of said housing.

14. The powder delivery device according to claim 1, wherein said device can be manipulated such that the spatial orientation of said barrel longitudinal axis can be disposed at up to about 90° below the horizontal without adverse impact upon the operability of the device.

15. The powder delivery device according to claim 14, wherein said barrel longitudinal can be disposed between about 20° and about 70° below the horizontal without adverse impact upon the operability of the device.

16. The powder delivery device according to claim 1, wherein said opposing, spaced, diametrically opposed openings in said elongate hollow member comprise axially aligned longitudinal slots.

17. The powder delivery device according to claim 1, wherein said shaft of said barrel portion includes an inner wall, and a portion of said inner wall adjacent to said open end of said shaft slopes gradually radially inwardly and then gradually radially outwardly along its axial length so as to create a diffusion portion adjacent said open end of said shaft of said barrel portion whereby the characteristics of an output powder spray may be controlled according to the relationship between the dimensions of said portion of said inner wall of said shaft adjacent to said open end of said barrel portion of said housing and the diameter of the portion of said shaft of said barrel portion located immediately inwardly of said shaft portion adjacent to said open end of said barrel portion.

18. A powder delivery device, comprising:

a powdered material reservoir defining an internal volume adapted to receive and store a quantity of powdered material, said reservoir including an elongate body, said body having a reservoir longitudinal axis, a closed outer end and an open inner end; and a substantially pistol-shaped housing, said housing including a handle portion, a barrel portion and a connecting portion between said handle portion and said barrel portion;

said handle portion including a generally elliptical, hollow bulb formed of a resilient material mounted in a support structure;

said bulb comprising in aligned relation along a bulb longitudinal axis a first end portion and a second end portion connected by a hollow, thin-walled portion;

said first end portion having a first length, a first peripheral cross-section perpendicular to said first length and defining an open ended first passageway centered on said bulb longitudinal axis;

said second end portion having a second length longer than said first length, a second peripheral cross-section of similar maximum diameter to said first peripheral cross-section, and defining a second passageway centered along said bulb longitudinal axis containing a one-way valve so oriented as to allow passage through said second passageway only in an axial direction toward said first passageway in said first end portion; and said thin-walled portion defining a symmetrical cavity centered on said bulb longitudinal axis having a substantially truncated elliptical cross-section measured in a plane containing said bulb longitudinal axis, and said support structure comprising a rear wall connecting said connecting portion to a pocket at an outer end of said rear wall adapted to receive and hold said second end portion of said bulb with said second passageway in said second end portion aligned with an opening formed at the base of said pocket, and walls extending from a side of said connecting portion substantially opposite said receptacle adapted to receive an hold at least a front part of said first portion of said bulb such that said first passageway therein is in communication with said internal conduit means in said connecting portion;

whereby said thin-walled portion of said bulb defines front, left and right sides of said handle portion such that said symmetrical cavity of said bulb can be collapsed by a user's hand grasping said handle portion of said device forcing a content of said symmetrical cavity of said bulb into said reservoir through said connecting portion, and whereby after collapse, said bulb is selectively restored to its non-collapsed configuration upon the release of said force by the resilience of said resilient material in combination with a content input into said thin-walled portion selectively received through said second passageway;

said barrel portion defining an open ended, elongate, hollow shaft centered on a barrel longitudinal axis, said shaft opening to the atmosphere at said open end thereof and opening into said connecting portion at the other end thereof; and said connecting portion defining a receptacle adapted to securely, sealingly and removably receive said open end of said reservoir and to hold said reservoir longitudinal axis at a rearwardly extending upward angle relative to said barrel longitudinal axis substantially opposite to said handle portion; including internal conduit means joining said first outlet of said handle portion to a second inlet located in said receptacle; and including an elongate, hollow element extending through a second outlet in said receptacle so as to open at one end into an end of a passageway in said connecting portion that opens at its other end into said shaft of said barrel portion, and also extending outwardly from said second outlet at substantially the same angle to said barrel longitudinal axis as said reservoir longitudinal axis when said reservoir is mounted in said receptacle to an open end, said outwardly extending portion of said elongate, hollow member further defining a plurality of opposed longitudinal slots at spaced intervals along its length;

whereby, when said internal volume of said reservoir contains a quantity of powdered material and said reservoir is mounted in said receptacle, a collapse of said bulb causes a content of said bulb to be forced into said internal volume of said reservoir in the form of a pulse so as to aerosolize a portion said powdered material stored in said reservoir and to cause at least some of said aerosolized powdered material to be discharged from said open end of said barrel portion via said open end and said longitudinal slots in said elongate, hollow member, said internal passageway of said connecting portion and said shaft of said barrel portion.

19. The powder delivery device according to claim 18, wherein said shaft of said barrel portion includes an inner wall, and a portion of said inner wall adjacent to said open end of said shaft slopes gradually radially inwardly and then gradually radially outwardly along its axial length so as to create a diffusion portion adjacent said open end of said shaft of said barrel portion whereby the characteristics of an output powder spray may be controlled according to the relationship between the dimensions of said portion of said inner wall of said shaft adjacent to said open end of said barrel portion of said housing and the diameter of the portion of said shaft of said barrel portion located immediately inwardly of said shaft portion adjacent to said open end of said barrel portion.

20. The powder delivery device according to claim 18 further comprising:

an open ended, elongate cannula associated with said barrel portion of said housing defining an open lumen extending therethrough, said cannula having a substantially constant internal diameter centered on a cannula longitudinal axis, including a first portion adjacent to an inlet one of said open ends substantially fixedly disposed within said elongate, hollow shaft of said barrel portion of said housing with said cannula longitudinal axis substantially aligned with said barrel longitudinal axis, and including a second portion adjacent an outlet one of said open ends projecting outwardly from said open end of said shaft of said barrel portion of said housing; and a diffuser associated with said outlet open end of said cannula, said diffuser defining an extension of said lumen of said cannula the diameter of which gradually narrows and thereafter gradually widens as it extends outwardly from said outlet open end of said cannula so as to achieve a desired spray pattern exiting from said powder delivery device as measured at a preferred spray initiation distance from a target surface.

21. A powder delivery device, comprising:

a powdered material reservoir defining an internal volume adapted to receive and store a quantity of powdered material, said reservoir including an elongate body, said body having a reservoir longitudinal axis, a closed outer end and an open inner end; and a substantially pistol-shaped housing, said housing including a handle portion, a barrel portion and a connecting portion between said handle portion and said barrel portion;

said handle portion including a generally elliptical, hollow bulb formed of a resilient material mounted in a support structure;

said bulb comprising in aligned relation along a bulb longitudinal axis a first end portion and a second end portion connected by a hollow, thin-walled portion;

said first end portion having a first length, a first peripheral cross-section perpendicular to said first length and defining an open ended first passageway centered on said bulb longitudinal axis;

said second end portion having a second length longer than said first length, a second peripheral cross-section of similar maximum diameter to said first peripheral cross-section, and defining a second passageway centered along said bulb longitudinal axis containing a one-way valve so oriented as to allow passage through said second passageway only in an axial direction toward said first passageway in said first end portion; and said thin-walled portion defining a symmetrical cavity centered on said bulb longitudinal axis having a substantially truncated elliptical cross-section measured in a plane containing said bulb longitudinal axis, and said support structure comprising a rear wall connecting said connecting portion to a pocket at an outer end of said rear wall adapted to receive and hold said second end portion of said bulb with said second passageway in said second end portion aligned with an opening formed at the base of said pocket, and walls extending from a side of said connecting portion opposite said receptacle adapted to receive an hold at least a front part of said first portion of said bulb such that said first passageway therein is in communication with said internal conduit means in said connecting portion;

whereby said thin-walled portion of said bulb defines front, left and right sides of said handle portion such that said symmetrical cavity of said bulb can be collapsed by a user's hand grasping said handle portion of said device forcing a content of said symmetrical cavity of said bulb into said reservoir through said connecting portion, and whereby after collapse, said bulb is selectively restored to its non-collapsed configuration upon the release of said force by the resilience of said resilient material in combination with a content input into said thin-walled portion selectively received through said second passageway;

said barrel portion defining an open ended, elongate, hollow shaft centered on a barrel longitudinal axis, said shaft opening to the atmosphere at said open end thereof and opening into said connecting portion at the other end thereof; and said connecting portion including:

(i) a receptacle adapted to securely, sealingly and removably receive said open end of said reservoir and to hold said reservoir with its reservoir longitudinal axis disposed at a rearwardly extending upward angle relative to said barrel longitudinal axis of said barrel portion opposite to said handle portion, said receptacle including;

(a) an outer cavity having a sidewall including a lower edge, an annular base extending radially inwardly from said lower edge of said sidewall, and an inner wall portion extending axially outwardly from an inner edge of said annular base substantially parallel to, but a distance shorter than the smallest axial dimension of, said sidewall such that an axially outwardly facing open groove is located adjacent to said base in said connecting portion of said housing, said sidewall of said cavity defines a substantially circular cross-sectional area, and said outer cavity is adapted to receive said open end of said reservoir in said groove and to support said reservoir in said connecting portion of said housing such that said reservoir longitudinal axis is disposed at about 45° to said barrel longitudinal axis, and (b) an inner cavity extending axially inwardly from an inner periphery of said base of said outer cavity, said inner cavity having a radially inwardly curved sidewall connecting said inner periphery of said base to a substantially flat bottom portion, wherein said second inlet enters said receptacle through said bottom portion of said inner cavity and said second outlet exits said inner cavity through said curved sidewall at a position located substantially vertically upwardly relative to said second inlet opposite said handle portion of said housing;

(ii) internal conduit means joining said first outlet of said handle portion to a second inlet located in said receptacle; and (iii) an elongate, hollow element extending through a second outlet in said receptacle so as to open at one end into an end of a passageway in said connecting portion that opens at its other end into said shaft of said barrel portion, and also extending outwardly from said second outlet at substantially the same angle to said barrel longitudinal axis as said reservoir longitudinal axis when said reservoir is mounted in said receptacle to an open end, said outwardly extending portion of said elongate, hollow member further defining a plurality of opposed longitudinal slots at spaced intervals along its length;

whereby, when said internal volume of said reservoir contains a quantity of powdered material and said reservoir is mounted in said receptacle, a collapse of said bulb causes a content of said bulb to be forced into said internal volume of said reservoir in the form of a pulse so as to aerosolize a portion said powdered material stored in said reservoir and to cause at least some of said aerosolized powdered material to be discharged from said open end of said barrel portion via said open end and said longitudinal slots in said elongate, hollow member, said internal passageway of said connecting portion and said shaft of said barrel portion.

22. The powder delivery device according to claim 21, wherein said shaft of said barrel portion includes an inner wall, and a portion of said inner wall adjacent to said open end of said shaft slopes gradually radially inwardly and then gradually radially outwardly along its axial length so as to create a diffusion portion adjacent said open end of said shaft of said barrel portion whereby the characteristics of an output powder spray may be controlled according to the relationship between the dimensions of said portion of said inner wall of said shaft adjacent to said open end of said barrel portion of said housing and the diameter of the portion of said shaft of said barrel portion located immediately inwardly of said shaft portion adjacent to said open end of said barrel portion.

23. The powder delivery device according to claim 21 further comprising:

an open ended, elongate cannula associated with said barrel portion of said housing defining an open lumen extending therethrough, said cannula having a substantially constant internal diameter centered on a cannula longitudinal axis, including a first portion adjacent to an inlet one of said open ends substantially fixedly disposed within said elongate, hollow shaft of said barrel portion of said housing with said cannula longitudinal axis substantially aligned with said barrel longitudinal axis, and including a second portion adjacent an outlet one of said open ends projecting outwardly from said open end of said shaft of said barrel portion of said housing; and a diffuser associated with said outlet open end of said cannula, said diffuser defining an extension of said lumen of said cannula the diameter of which gradually narrows and thereafter gradually widens as it extends outwardly from said outlet open end of said cannula so as to achieve a desired spray pattern exiting from said powder delivery device as measured at a preferred spray initiation distance from a target surface.

* * * * *